(12) United States Patent
Di Paola et al.

(10) Patent No.: US 11,031,729 B2
(45) Date of Patent: Jun. 8, 2021

(54) BLOOD PUMP CONNECTORS

(71) Applicant: TC1 LLC, St. Paul, MN (US)

(72) Inventors: John Mark Di Paola, Livermore, CA (US); Michael McCoy, St. Paul, MN (US); John Duc Nguyen, San Ramon, CA (US); Jaime Romero, San Leandro, CA (US); Dustin Roelle, Mountain House, CA (US); Andrew Wong, St. Paul, MN (US); Dmitry Protsenko, St. Paul, MN (US); Michael Sahines, St. Paul, MN (US)

(73) Assignee: TC1 LLC, St. Paul, MN (US)

( * ) Notice: Subject to any disclaimer, the term of this patent is extended or adjusted under 35 U.S.C. 154(b) by 124 days.

(21) Appl. No.: 16/395,134

(22) Filed: Apr. 25, 2019

(65) Prior Publication Data

US 2019/0334283 A1      Oct. 31, 2019

Related U.S. Application Data

(60) Provisional application No. 62/664,679, filed on Apr. 30, 2018, provisional application No. 62/736,267, (Continued)

(51) Int. Cl.
*A61M 60/50* (2021.01)
*H01R 13/629* (2006.01)
(Continued)

(52) U.S. Cl.
CPC ....... *H01R 13/62927* (2013.01); *A61M 60/50* (2021.01); *A61M 60/871* (2021.01);
(Continued)

(58) Field of Classification Search
CPC .... A61M 1/1086; A61M 1/122; A61M 1/127; F04B 17/03; F04B 19/04; F04B 2203/00;
(Continued)

(56) References Cited

U.S. PATENT DOCUMENTS

| | | |
|---|---|---|
| 3,882,861 A | 5/1975 | Kettering et al. |
| 4,521,871 A | 6/1985 | Galdun et al. |

(Continued)

FOREIGN PATENT DOCUMENTS

| | | |
|---|---|---|
| DE | 19735151 A1 | 2/1998 |
| EP | 1 812 094 A | 5/2006 |

(Continued)

OTHER PUBLICATIONS

"Berlin Heart Incor", My LVAD, Available online at:http://www.mylvad.com/content/berlin-heart-incor, Jul. 16, 2015, 3 pages.

(Continued)

*Primary Examiner* — George Manuel
(74) *Attorney, Agent, or Firm* — Kilpatrick Townsend & Stockton LLP

(57) ABSTRACT

An implantable blood pump system is disclosed herein. The implantable blood pump system includes an implantable blood pump, a controller coupled to the blood pump, a connector receptacle, and a connector insert. The connector receptacle can include a plurality of contacts, and a following surface. The connector insert can be received within the connector receptacle to couple a plurality of insert contacts with the plurality of contacts of the connector receptacle. The connector insert can include walls defining a follower receptacle that can receive a portion of the following surface when the connector insert is in a desired alignment with respect to the connector receptacle, and a cam surface that can engage with the following surface to bias the connector insert to the desired alignment with respect to the connector receptacle when the connector insert is inserted into the connector receptacle.

26 Claims, 20 Drawing Sheets

Related U.S. Application Data filed on Sep. 25, 2018, provisional application No. 62/783,606, filed on Dec. 21, 2018.

(51) Int. Cl.

| | |
|---|---|
| *F04B 17/03* | (2006.01) |
| *F04B 19/04* | (2006.01) |
| *H01R 13/52* | (2006.01) |
| *H01R 13/627* | (2006.01) |
| *H01R 24/28* | (2011.01) |
| *H01R 24/86* | (2011.01) |
| *H01R 25/00* | (2006.01) |
| *H01R 43/26* | (2006.01) |
| *A61M 60/871* | (2021.01) |
| *H01R 103/00* | (2006.01) |

(52) U.S. Cl.
CPC .............. *F04B 17/03* (2013.01); *F04B 19/04* (2013.01); *H01R 13/5219* (2013.01); *H01R 13/5224* (2013.01); *H01R 13/5227* (2013.01); *H01R 13/6273* (2013.01); *H01R 24/28* (2013.01); *H01R 24/86* (2013.01); *H01R 25/006* (2013.01); *H01R 43/26* (2013.01); *F04B 2203/00* (2013.01); *H01R 2103/00* (2013.01)

(58) Field of Classification Search
CPC ............ H01R 13/5219; H01R 13/5224; H01R 13/5227; H01R 13/6273; H01R 13/62927; H01R 2103/00; H01R 24/28; H01R 24/86; H01R 25/006; H01R 43/26
See application file for complete search history.

(56) References Cited

U.S. PATENT DOCUMENTS

| | | |
|---|---|---|
| 5,046,965 A | 9/1991 | Neese et al. |
| 5,695,471 A | 12/1997 | Wampler |
| 5,695,474 A | 12/1997 | Daugherty |
| 5,888,242 A | 3/1999 | Antaki et al. |
| 5,935,105 A | 8/1999 | Manning et al. |
| 5,991,595 A | 11/1999 | Romano et al. |
| 6,071,093 A | 6/2000 | Hart |
| 6,116,862 A | 9/2000 | Rau et al. |
| 6,146,179 A | 11/2000 | Denny et al. |
| 6,183,412 B1 | 2/2001 | Benkowski et al. |
| 6,186,665 B1 | 2/2001 | Maher et al. |
| 6,234,772 B1 | 5/2001 | Wampler et al. |
| 6,264,635 B1 | 7/2001 | Wampler et al. |
| 6,305,962 B1 | 10/2001 | Maher et al. |
| 6,494,736 B2 | 12/2002 | Mito |
| 6,592,620 B1 | 7/2003 | Lancisi et al. |
| 6,688,861 B2 | 2/2004 | Wampler |
| 6,991,595 B2 | 1/2006 | Burke et al. |
| 7,340,304 B2 | 3/2008 | MacDonald et al. |
| 7,425,142 B1 | 9/2008 | Putz |
| 7,658,613 B1 | 2/2010 | Griffin et al. |
| 7,699,586 B2 | 4/2010 | LaRose et al. |
| 7,961,156 B2 | 6/2011 | Knott et al. |
| 7,976,271 B2 | 7/2011 | LaRose et al. |
| 7,997,854 B2 | 8/2011 | LaRose et al. |
| 8,007,254 B2 | 8/2011 | LaRose et al. |
| 8,029,441 B2 | 10/2011 | Mazza et al. |
| 8,152,493 B2 | 4/2012 | LaRose et al. |
| 8,157,720 B2 | 4/2012 | Marseille et al. |
| 8,186,665 B2 | 5/2012 | Akema |
| 8,200,335 B2 | 6/2012 | Donofrio et al. |
| 8,323,174 B2 | 12/2012 | Jeevanandam et al. |
| 8,344,847 B2 | 1/2013 | Moberg et al. |
| 8,348,678 B2 | 1/2013 | Hardisty et al. |
| 8,449,444 B2 | 5/2013 | Poirier |
| 8,506,471 B2 | 8/2013 | Bourque |
| 8,562,508 B2 | 10/2013 | Dague et al. |
| 8,597,350 B2 | 12/2013 | Rudser et al. |
| 8,628,460 B2 | 1/2014 | Yomtov et al. |
| 8,639,348 B2 | 1/2014 | Geheb |
| 8,652,024 B1 | 2/2014 | Yanai et al. |
| 8,657,733 B2 | 2/2014 | Ayre et al. |
| 8,668,473 B2 | 3/2014 | LaRose et al. |
| 8,684,763 B2 | 4/2014 | Mattson et al. |
| 8,894,561 B2 | 11/2014 | Callaway et al. |
| 8,971,958 B2 | 3/2015 | Frikart et al. |
| 9,302,035 B2 | 4/2016 | Marseille et al. |
| 9,985,374 B2 | 5/2018 | Hodges |
| 10,124,101 B2 | 11/2018 | Wong et al. |
| 2002/0007198 A1 | 1/2002 | Haupert et al. |
| 2005/0071001 A1 | 3/2005 | Jarvik |
| 2007/0078293 A1 | 4/2007 | Shambaugh, Jr. et al. |
| 2007/0142696 A1 | 6/2007 | Crosby et al. |
| 2008/0021394 A1 | 1/2008 | LaRose et al. |
| 2008/0207042 A1 | 8/2008 | Schmidt et al. |
| 2009/0118827 A1 | 5/2009 | Sugiura |
| 2009/0203957 A1 | 8/2009 | LaRose et al. |
| 2011/0152600 A1 | 6/2011 | Scott et al. |
| 2011/0160516 A1 | 6/2011 | Dague et al. |
| 2011/0218383 A1 | 9/2011 | Broen et al. |
| 2012/0028490 A1 | 2/2012 | Litzler et al. |
| 2012/0046514 A1 | 2/2012 | Bourque |
| 2012/0095281 A1 | 4/2012 | Reichenbach et al. |
| 2012/0172657 A1 | 7/2012 | Marseille et al. |
| 2012/0183261 A1 | 7/2012 | Schwandt et al. |
| 2013/0096364 A1 | 4/2013 | Reichenbach et al. |
| 2013/0121821 A1 | 5/2013 | Ozaki et al. |
| 2013/0127253 A1 | 5/2013 | Stark et al. |
| 2013/0170970 A1 | 7/2013 | Ozaki et al. |
| 2013/0225909 A1 | 8/2013 | Dormanen et al. |
| 2013/0314047 A1 | 11/2013 | Eagle et al. |
| 2014/0073838 A1* | 3/2014 | Dague .................. A61M 1/127 600/16 |
| 2014/0194985 A1 | 7/2014 | Vadala, Jr. |
| 2014/0243970 A1 | 8/2014 | Yanai |
| 2014/0309733 A1 | 10/2014 | Cotter et al. |
| 2015/0038771 A1 | 2/2015 | Marseille et al. |
| 2016/0095968 A1 | 4/2016 | Rudser |
| 2017/0062978 A1* | 3/2017 | Seido ............... H01R 13/62922 |
| 2018/0055983 A1 | 3/2018 | Bourque |
| 2018/0250459 A1 | 9/2018 | Kimball et al. |
| 2018/0256796 A1 | 9/2018 | Hansen |
| 2018/0256800 A1 | 9/2018 | Conyers et al. |
| 2018/0256801 A1 | 9/2018 | Conyers et al. |
| 2019/0290816 A1 | 9/2019 | Petersen |

FOREIGN PATENT DOCUMENTS

| | | |
|---|---|---|
| WO | 2006055745 A2 | 5/2006 |
| WO | 2010122139 A1 | 10/2010 |
| WO | 2011081626 A1 | 7/2011 |
| WO | 2014107424 A2 | 7/2014 |
| WO | 2015017770 A1 | 5/2015 |
| WO | 2017087380 A1 | 5/2017 |

OTHER PUBLICATIONS

"The HeartMate II System", HeartMate II, Left Ventricular Assist System, Available online at: http://heartmateii.com/heartmate-ii-system.aspx, Jul. 16, 2015, 2 pages.

* cited by examiner

BLOOD PUMP CONNECTORS

CROSS REFERENCE TO RELATED APPLICATIONS

The present application claims the benefit under 35 USC § 119(e) of U.S. Provisional Appln. No. 62/664,679 filed Apr. 30, 2018; 62/736,267 filed Sep. 25, 2018; and 62/783,606 filed Dec. 21, 2018; the full disclosures which are incorporated herein by reference in their entirety for all purposes.

BACKGROUND

This application relates generally to mechanical circulatory support systems. Ventricular assist devices, known as VADs, are implantable blood pumps used for both short-term (i.e., days, months) and long-term applications (i.e., years or a lifetime) where a patient's heart is incapable of providing adequate circulation, commonly referred to as heart failure or congestive heart failure. According to the American Heart Association, more than five million Americans are living with heart failure, with about 670,000 new cases diagnosed every year. People with heart failure often have shortness of breath and fatigue. Years of living with blocked arteries or high blood pressure can leave your heart too weak to pump enough blood to your body. As symptoms worsen, advanced heart failure develops.

A patient suffering from heart failure, also called congestive heart failure, may use a VAD while awaiting a heart transplant or as a long term destination therapy. In another example, a patient may use a VAD while recovering from heart surgery. Thus, a VAD can supplement a weak heart (i.e., partial support) or can effectively replace the natural heart's function. VADs can be implanted in the patient's body and powered by an electrical power source inside or outside the patient's body.

Operation of a VAD can be controlled and/or affected by a controller communicatingly coupled with the VAD. The controller can be an external controller or an implanted controller. The operation of the controller can be important to the operation of the VAD and can control all or portions of the operation of the VAD including, for example, a speed of the VAD. Some controllers, for example, can monitor one or several parameters relevant to the patient and can affect operation of the VAD according to those one or several monitored parameters. This can include, for example, changing the VAD speed in response to an increase or decrease in physical activity, or the like. Controllers are typically connected to the VAD via a wired connection. Additionally, some controllers are connected to one or more power sources via a wired connection. The connectors in these wired connections may be improved to facilitate ease of use and to improve durability. Accordingly, new systems, methods, and/or connectors are desired.

BRIEF SUMMARY

The present disclosure relates to systems and devices for increasing the ruggedization of a mechanical circulatory support system. This system can include a connector that can include a connector receptacle and a connector insert, each of which can include electrical contacts that can mate when the connector insert is received within the connector receptacle. The connector receptacle and the connector insert can include features that can protect electrical contacts via sealing around electrical contacts and/or that can protect electrical contacts by facilitating draining of fluid from the connector receptacle when the connector insert is inserted into the connector receptacle. In some embodiments, the connector insert and/or the connector receptacle can be sized and shaped such that the connector insert can be inserted into the connector receptacle in one of a finite number of orientations such as, for example, a first orientation and second orientation.

In some aspects, the connector can include the connector receptacle and the connector insert. One or both of the connector receptacle and the connector insert can include features that can automatically bring the connector receptacle and the connector insert to a desired relative alignment and/or orientation as the connector insert is advanced into the connector receptacle. For example, the connector receptacle can include one or several orientation features that can engage with one or several mating features of the connector insert when the connector insert is advanced into the connector receptacle. The interaction between the orientation features and the mating features can cause the connector insert to relatively reorient itself to a desired relative orientation when the connector insert is inserted into the connector receptacle.

One aspect of the present disclosure relates to an implantable blood pump system. The implantable blood pump system can include: an implantable blood pump, a controller coupled to the blood pump, a connector receptacle, and a connector insert. The connector receptacle can include: a plurality of contacts and a following surface. In some embodiments, the connector insert can be received within the connector receptacle to couple a plurality of insert contacts with the plurality of contacts of the connector receptacle. The connector insert can include: walls defining a follower receptacle that can receive a portion of the following surface when the connector insert is in a desired alignment with respect to the connector receptacle, and a cam surface that can engage with the following surface to bias the connector insert to the desired alignment with respect to the connector receptacle when the connector insert is inserted into the connector receptacle.

In some embodiments, the connector receptacle is located in the controller, and in some embodiments, the connector receptacle is located in blood pump. In some embodiments, the following surface can be a key. In some embodiments, the connector receptacle can include a side and a recessed bottom. In some embodiments, the connector receptacle can define a receptacle volume having an opening. In some embodiments, the following surface can extend from the side of the connector receptacle. In some embodiments, the following surface can be a key having a pointed tip directed towards the opening of the receptacle volume. In some embodiments, the key can include a first key and a second key.

In some embodiments, the cam surface can include a pair of inclined planes extending around at least a portion of an exterior of the connector insert. In some embodiments, each of the pair of inclined planes terminates at one or the walls defining the follower receptacle. In some embodiments, the pair of inclined planes comprises a first pair of inclined planes and a second pair of inclined planes. In some embodiments, the first pair of inclined planes meet the second pair of inclined planes at a first point and a second point.

In some embodiments, the cam surface and the following surface can be designed such that following surface is at least partially received in the follower receptacle before any of the plurality of insert contacts engage any of the plurality of contacts of the connector receptacle. In some embodiments, the implantable blood pump system can include a seal extending around the receptacle connector, which seal can seal with the connector insert when the connector insert is received within the connector receptacle.

In some embodiments, the connector insert further includes a locking mechanism. In some embodiments, the locking mechanism can include at least one locking feature and at least one control feature coupled to the at least one locking feature. In some embodiments, the at least one locking feature can include a wedge-shaped member. In some embodiments, the at least one control feature can include a button.

In some embodiments, the at least one locking feature includes an abutting surface. In some embodiments, the connector receptacle can include a securement feature including a depression and a stop wall. In some embodiments, the stop wall can engage the abutting surface of the locking mechanism when the connector insert is received within the connector receptacle.

In some embodiments, the implantable blood pump system includes a locking member extending at least partially around the connector receptacle. In some embodiments, the locking member includes a channel in which the connector receptacle is at least partially received. In some embodiments, the locking member is rotatable about the connector receptacle. In some embodiments, the locking member selectively engages with the following surface of the connector insert to retain the at least a portion of the following surface within the follower receptacle. In some embodiments, the following surface includes a key and a circular cylindrical member extending from a side of the connector insert.

In some embodiments, the locking member includes a blocking feature that can engage with at least a portion of the following surface to prevent retraction of the connector insert from the connector receptacle. In some embodiments, the locking member includes a biasing feature that can bias the blocking feature to engage with the at least a portion of the following surface. In some embodiments, the blocking feature engages with the circular cylindrical member. In some embodiments, the biasing feature includes a compliant member that can deflect to allow the blocking feature to engage and disengage with the at least a portion of the following surface. In some embodiments, the inserting of the connector insert into the connector receptacle deflects the compliant member and rotates the locking member about the connector receptacle.

One aspect of the present disclosure relates to a medical device. The medical device can include: a housing having an external surface defining an internal volume, and a connector receptacle located in the housing. The connector receptacle can receive a connector insert. The connector receptacle can include a side wall extending from the external surface of the housing into the internal volume and to a bottom of the connector receptacle. In some embodiments, the side wall and the bottom together define a receptacle volume having an opening proximate to the external surface of the housing. The connector receptacle can include a plurality of electrical contacts that mate with corresponding contacts of a connector insert when the connector insert is coupled with the connector receptacle. The connector receptacle can include an orientation feature that engages with at least one mating feature of the connector insert to move the connector insert to a desired alignment with respect to the connector receptacle while the connector insert is inserted into the connector receptacle.

In some embodiments, the orientation feature can be a key extending from the side wall into the receptacle volume. In some embodiments, the key can engage an alignment cam on the connector insert. In some embodiments, the key can be received within a key slot on the connector insert when the connector insert is at the desired alignment with respect to the connector receptacle and fully received within the receptacle volume. In some embodiments, the key can be a pointed key having a point. In some embodiments, the point of the pointed key engages with the alignment cam when the connector insert is inserted into the connector receptacle.

In some embodiments, the plurality of electrical contacts are on the bottom of the connector receptacle. In some embodiments, the plurality of electrical contacts are arranged in a ring on the bottom of the connector receptacle. In some embodiments, the medical device can include a seal that can sealingly mate with at least a portion of the connector insert when the connector insert is received within the connector receptacle. In some embodiments, the medical device can include a seal that can provide an environmental barrier when mating with at least a portion of the connector insert when the connector insert is received within the connector receptacle. In some embodiments, the seal extends around the opening of the receptacle volume. In some embodiments, the medical device can be at least one of: a controller; an implantable blood pump; and a power source.

One aspect of the present disclosure relates to a method of coupling an implantable blood pump system. The method includes: contacting a mating feature of a connector insert to an orientation feature of a connector receptacle, advancing the connector insert into the connector receptacle, reorienting the connector insert from the first orientation to a second orientation via interaction between the orientation feature of the connector receptacle and the mating feature of the connector insert as the connector insert advances into the connector receptacle, and mating insert contacts with connector contacts. In some embodiments, the connector insert has a first orientation when advanced into the connector receptacle.

In some embodiments, the orientation feature can include a key extending from the side wall into the receptacle volume. In some embodiments, the key can engage an alignment cam on the connector insert. In some embodiments, the method includes receiving a key in a key slot on the connector insert when the connector insert is reoriented to the second orientation. In some embodiments, the key can be a pointed key having a point. In some embodiments, the point of the pointed key interacts with the mating feature of the connector insert to reorient the connector insert from the first orientation to the second orientation.

In some embodiments, the mating feature includes a pair of inclined planes wrapping around at least a portion of an exterior of the connector insert. In some embodiments, the pair of inclined planes includes a first inclined plane having a positive slope and a second inclined plane having a negative slope. In some embodiments, each of the first inclined plane and the second inclined plane terminates at the key slot.

One aspect of the present disclosure relates to an implantable blood pump system. The implantable blood pump system includes: an implantable blood pump, a controller coupled to the blood pump, a connector insert including a plurality of insert contacts, and a connector receptacle located in a housing and including a plurality of contacts that can mate with the insert contacts of the connector insert. In some embodiments, the connector insert is sealed. In some embodiments, the connector receptacle can receive the connector insert. In some embodiments, the connector receptacle can include a drain feature that can allow draining of any liquid in the connector receptacle when the connector insert is received within the connector receptacle.

In some embodiments, the housing is a part of one of: the controller; the implantable blood pump; and an external power source. In some embodiments, the connector receptacle includes a top, a recessed base positioned at a depth below the top of the connector receptacle, and a sidewall extending from the top to the recessed base. In some embodiments, the plurality of contacts are arranged on the recessed base. In some embodiments, the drain feature can be a channel. In some embodiments, the connector receptacle is positioned between sides of the housing, and wherein the housing defines the channel. In some embodiments, the channel extends through the sides of the housing. In some embodiments, the channel has a channel depth below the top of the connector receptacle equal to the depth of the connector receptacle.

In some embodiments, the plurality of contacts includes at least four electrical contacts and an optical connector. In some embodiments, the at least four electrical contacts include two positive contacts and two negative contacts. In some embodiments, the connector receptacle can receive the connector insert in one of a finite number of positions. In some embodiments, the plurality of contacts are arranged to connect with mating contacts of the connector insert when the connector insert is received by the connector receptacle in any of the finite number of positions. In some embodiments, the connector receptacle can receive the connector insert in one of a first orientation and a second orientation. In some embodiments, the plurality of contacts can include at least two positive contacts and at least two negative contacts. In some embodiments, the plurality of contacts are positioned such that each of the positive contacts and the negative contacts mate with corresponding contacts of the connector insert when the connector insert is in either of the first orientation and the second orientation.

In some embodiments, the system can include a seal extending around at least one of the mating contacts of the connector insert. In some embodiments, the seal fluidly isolates one of the at least one of the mating contacts of the connector insert from others of the mating contacts of the connector insert when the connector insert is received within the connector receptacle and when the mating contacts mate with the contacts of the connector receptacle.

In some embodiments, the connector insert further includes a locking mechanism. In some embodiments, the locking mechanism can include at least one locking feature and at least one control feature coupled to the at least one locking feature. In some embodiments, the at least one locking feature can include a wedge-shaped member. In some embodiments, the at least one control feature can include a button.

In some embodiments, the at least one locking feature includes an abutting surface. In some embodiments, the connector receptacle can include a securement feature including a depression and a stop wall. In some embodiments, the stop wall can engage the abutting surface of the locking mechanism when the connector insert is received within the connector receptacle.

One aspect of the present disclosure relates to a method of coupling an implantable blood pump system. The method includes: inserting a connector insert into a connector receptacle located in a housing, draining fluid from the connector receptacle via a drain feature as the connector insert is inserted into the connector receptacle, and mating the insert contact to the receptacle contacts when the connector insert is inserted into the connector receptacle. In some embodiments, the connector receptacle can include receptacle contacts that can mate with insert contacts of the connector insert. In some embodiments, the connector receptacle can include a top, a recessed base positioned at a depth below the top of the connector receptacle, and a sidewall extending from the top to the recessed base. In some embodiments, the plurality of contacts are arranged on the recessed base.

In some embodiments, the connector insert can include a seal extending around at least one of the insert contacts of the connector insert. In some embodiments, each of the insert contact is surrounded by a seal. In some embodiments, the method can include compressing the seal between the connector insert and the connector receptacle to seal each insert contact and mated receptacle contact. In some embodiments, the seal fluidly isolates one of the at least one of the insert contacts of the connector insert from others of the insert contacts of the connector insert when the seal is compressed between the connector insert and the connector receptacle.

One aspect of the present disclosure relates to an implantable blood pump system. The implantable blood pump system includes: an implantable blood pump, a controller coupled to the blood pump, a connector insert, and a connector receptacle. The connector receptacle includes: a plurality of contacts, walls defining a follower receptacle, and a cam surface. The connector insert can be sized and shaped to be received within the connector receptacle to couple a plurality of insert contacts with the plurality of contacts of the connector receptacle. The connector insert can include a following surface. The following surface can engage with the cam surface to bias the connector insert to a desired alignment with respect to the connector receptacle when the connector insert is inserted into the connector receptacle. In some embodiments, at least a portion of the following surface can be received within the follower receptacle when the connector insert is in a desired alignment with respect to the connector receptacle.

In some embodiments, the implantable blood pump system includes a locking member extending at least partially around the connector receptacle. In some embodiments, the locking member can include a channel in which the connector receptacle is at least partially received. In some embodiments, the locking member is rotatable about the connector receptacle. In some embodiments, the locking member selectively engages with the following surface of the connector insert to retain the at least a portion of the following surface within the follower receptacle.

In some embodiments, the following surface includes a key and a circular cylindrical member extending from a side of the connector insert. In some embodiments, the locking member includes: a blocking feature that can engage with at least a portion of the following surface to prevent retraction of the connector insert from the connector receptacle, and a biasing feature that can bias the blocking feature to engage with the at least a portion of the following surface. In some embodiments, the blocking feature engages with the circular cylindrical member when the connector insert is received within the connector receptacle. In some embodiments, the biasing feature can be a compliant member that can deflect to allow the blocking feature to engage and disengage with the at least a portion of the following surface.

In some embodiments, the inserting of the connector insert into the connector receptacle deflects the compliant member and rotates the locking member about the connector receptacle. In some embodiments, the connector receptacle includes limiting features that engage with abutting features of the locking member to limit rotation of the locking member about the connector receptacle. In some embodiments, the locking member is coupled to the connector receptacle via a thrust washer. In some embodiments, the controller is coupled to the blood pump via a two piece driveline. In some embodiments, the connector receptacle is located at an end of a first piece of the two piece driveline and the connector insert is located at an end of a second piece of the two piece driveline.

In some embodiments, the coupling of the connector receptacle and the connector insert couples the controller to the blood pump. In some embodiments, the connector insert has an exterior side. In some embodiments, the following surface outwardly extends from the exterior side of the connector insert.

In some embodiments, the cam surface includes a pair of inclined planes extending along at least a portion of an end of the connector receptacle. In some embodiments, each of the pair of inclined planes terminates at one of the walls defining the follower receptacle. In some embodiments, the pair of inclined planes includes a first pair of inclined planes and a second pair of inclined planes. In some embodiments, the first pair of inclined planes meet the second pair of inclined planes at a first point and a second point. In some embodiments, the cam surface and the following surface are designed such that following surface is at least partially received in the follower receptacle before any of the plurality of insert contacts engage any of the plurality of contacts of the connector receptacle.

One aspect of the present disclosure relates to a method of coupling an implantable blood pump system. The method includes: contacting a following surface of a connector insert to an cam surface of a connector receptacle, advancing the connector insert into the connector receptacle, reorienting the connector insert from the first orientation to a second orientation via interaction between the cam surface of the connector receptacle and the following surface of the connector insert as the connector insert advances into the connector receptacle, rotating a locking member about the connector receptacle as the connector insert advances into the connector receptacle, mating insert contacts with connector contacts, and engaging the locking member with at least a portion of the following surface of the connector insert to retain the connector insert within the connector receptacle. In some embodiments, the connector insert has a first orientation when advanced into the connector receptacle.

In some embodiments, the locking member extends at least partially around the connector receptacle. In some embodiments, the connector receptacle is at least partially received within a channel of the locking member. In some embodiments, the locking member rotates about the connector receptacle as the connector insert is advanced into the connector receptacle. In some embodiments, the method includes receiving the following surface in a follower receptacle when the connector insert is reoriented to the second orientation. In some embodiments, the following surface can include a key and a circular cylindrical member extending from a side of the connector insert. In some embodiments, the method includes: rotating the locking member to disengage the locking member from the at least a portion of the following surface; and retracting the connector insert from the connector receptacle.

Further areas of applicability of the present disclosure will become apparent from the detailed description provided hereinafter. It should be understood that the detailed description and specific examples, while indicating various embodiments, are intended for purposes of illustration only and are not intended to necessarily limit the scope of the disclosure.

DETAILED DESCRIPTION

Figure 1:
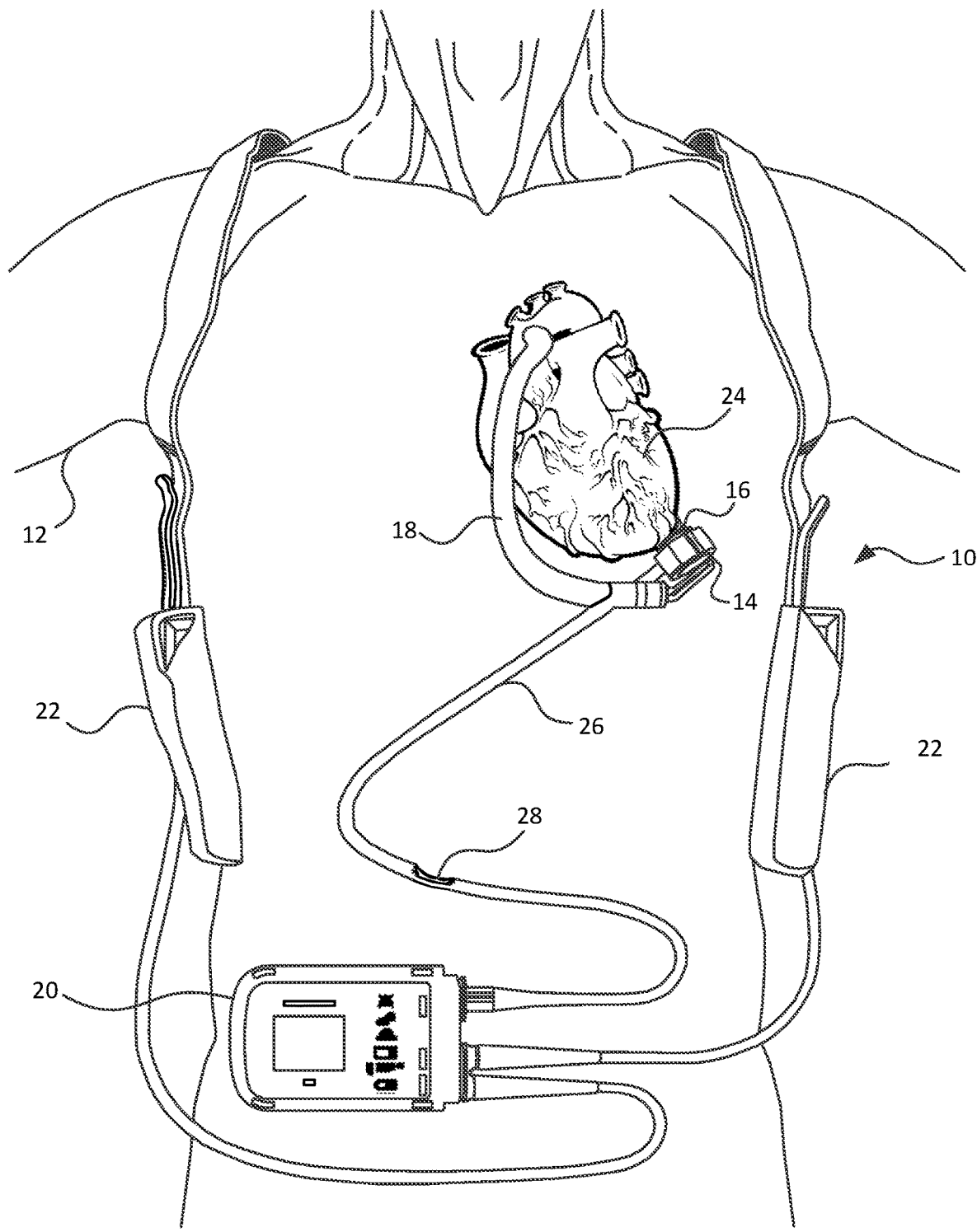
FIG. 1 is an illustration of a mechanical circulatory support system.

Circulatory support systems are increasingly used to support patient's blood circulation. These circulatory systems can include an implantable blood pump such as a VAD and a controller. In some embodiments, the controller can directly control the implantable blood pump via one or several control signals, and/or the controller can provide one or several parameters that can be used by the implantable blood pump to affect operation of the implantable blood pump, such as, for example, to change a speed of the implantable blood pump.

Due to this role of the controller in at least affecting operation of the implantable blood pump, reliability and ruggedness of the controller are important. However, in many instances controllers are coupled to either a power source such as an external power source or to the implantable blood pump via one or several cables, wires, drivelines, or the like. The connection of the controller with the other components relies on connectors that form this coupling. These connectors can be a weak spot in such circulatory system as connectors and the contacts that form part of connectors may be exposed to environmental factors that affect the ability of the connectors to reliably function over an extended time period. While numerous improvements have been made to connectors to minimize risk of damage to the connectors and to improve connector reliability, further improvements are desired.

Such improvements to the connectors may enhance the connector to minimize susceptibility to environmental factors, corrosion, and/or contamination of all or portions of the connector with foreign objects that may hinder coupling. Such improvements may further facilitate connecting the connector and may facilitate aligning the connector insert and the connector receptacle to improve connection. In some embodiments, for example, a connector may include one or several seals that seal contacts and/or that isolate contacts. In some embodiments, the connector can include one or several features that can facilitate draining of the connector of any fluid that may be in the connector at the time of coupling. In some embodiments, the connector can include one or several features that automatically align the connector when coupled and/or that facilitate coupling of the connector.

These features that facilitate alignment can include, for example, the shape of the connector insert and/or the connector receptacle. In some embodiments, for example, the connector insert can shaped and the connector receptacle can have a corresponding shape to allow insertion of the connector insert in one of a finite number of orientations into the connector receptacle. In one such embodiment, the connector insert can be oval-shaped and/or elongate and the connector receptacle can have a similar shape. In such an embodiment, this shape can allow insertion of the connector insert into the connector receptacle in one of two orientations. In some embodiments, the contacts in the connector receptacle and the contacts of the connector insert can be arranged to properly mate when the connector insert is inserted into the connector receptacle in any of the finite number of orientations.

With reference now to FIG. 1, an illustration of one embodiment a mechanical circulatory support system 10, also referred to herein as an implantable blood pump system 10, is shown. This mechanical circulatory support system 10 is partially implanted in a patient's body 12. The mechanical circulatory support system 10 comprises a implantable blood pump 14, ventricular cuff 16, outflow cannula 18, system controller 20, and external power sources 22. The implantable blood pump 14 may comprise a VAD that is attached to an apex of the left ventricle, as illustrated, or the right ventricle, or both ventricles of the heart 24. The VAD may comprise a centrifugal (as shown) or axial flow pump as described in further detail herein that is capable of pumping the entire output delivered to the left ventricle from the pulmonary circulation (i.e., up to 10 liters per minute). Related blood pumps applicable to the present invention are described in greater detail below and in U.S. Pat. Nos. 5,695,471, 6,071,093, 6,116,862, 6,186,665, 6,234,772, 6,264,635, 6,688,861, 7,699,586, 7,976,271, 7,997,854, 8,007,254, 8,152,493, 8,652,024, and 8,668,473 and U.S. Patent Publication Nos. 2007/0078293, 2008/0021394, 2009/0203957, 2012/0046514, 2012/0095281, 2013/0096364, 2013/0170970, 2013/0121821, and 2013/0225909, all of which are incorporated herein by reference for all purposes in their entirety.

The blood pump 14 may be attached to the heart 24 via the ventricular cuff 16 which is sewn to the heart 24 and coupled to the blood pump 14. The other end of the blood pump 14 connects to the ascending aorta via the outflow cannula 18 so that the VAD effectively diverts blood from the weakened ventricle and propels it to the aorta for circulation to the rest of the patient's vascular system.

In FIG. 1, the mechanical circulatory support system 10 is illustrated in the configuration in which powered operation is enabled via external power source 22. A driveline 26 which exits through the patient's abdomen 28, connects the implanted blood pump 14 to the system controller 20, which monitors system 10 operation. Related controller systems applicable to the present invention are described in greater detail below and in U.S. Pat. Nos. 5,888,242, 6,991,595, 8,323,174, 8,449,444, 8,506,471, 8,597,350, and 8,657,733 and U.S. Patent Publication Nos. 2005/0071001 and 2013/0314047, all of which are incorporated herein by reference for all purposes in their entirety.

The system may be powered by either one, two, or more external power sources 22. In some embodiments, one or several energy storage components, such as, for example, one or several batteries, in the controller 20 can power the mechanical circulatory support system 10. It will be appreciated that although the system controller 20 and power source 22 are illustrated outside/external to the patient body, the driveline 26, system controller 20 and/or power source 22 may be partially or fully implantable within the patient, as separate components or integrated with the blood bump 14. In some embodiments, for example, the system controller 20 can be implanted within the patient's body, and can receive power from a power source 22 that can be external to the patient's body. In some embodiments, this power can be provided to the controller 20 via a wired or wireless connection between the controller 20 and the power source 22. In some embodiments, this wireless connection can comprise a transcutaneous energy transfer system (TETS) that can, for example, include one or several resonant circuits. Examples of such modifications are further described in U.S. Pat. No. 8,562,508 and U.S. Patent Publication No. 2013/0127253, all of which are incorporated herein by reference for all purposes in their entirety.

Figure 2:
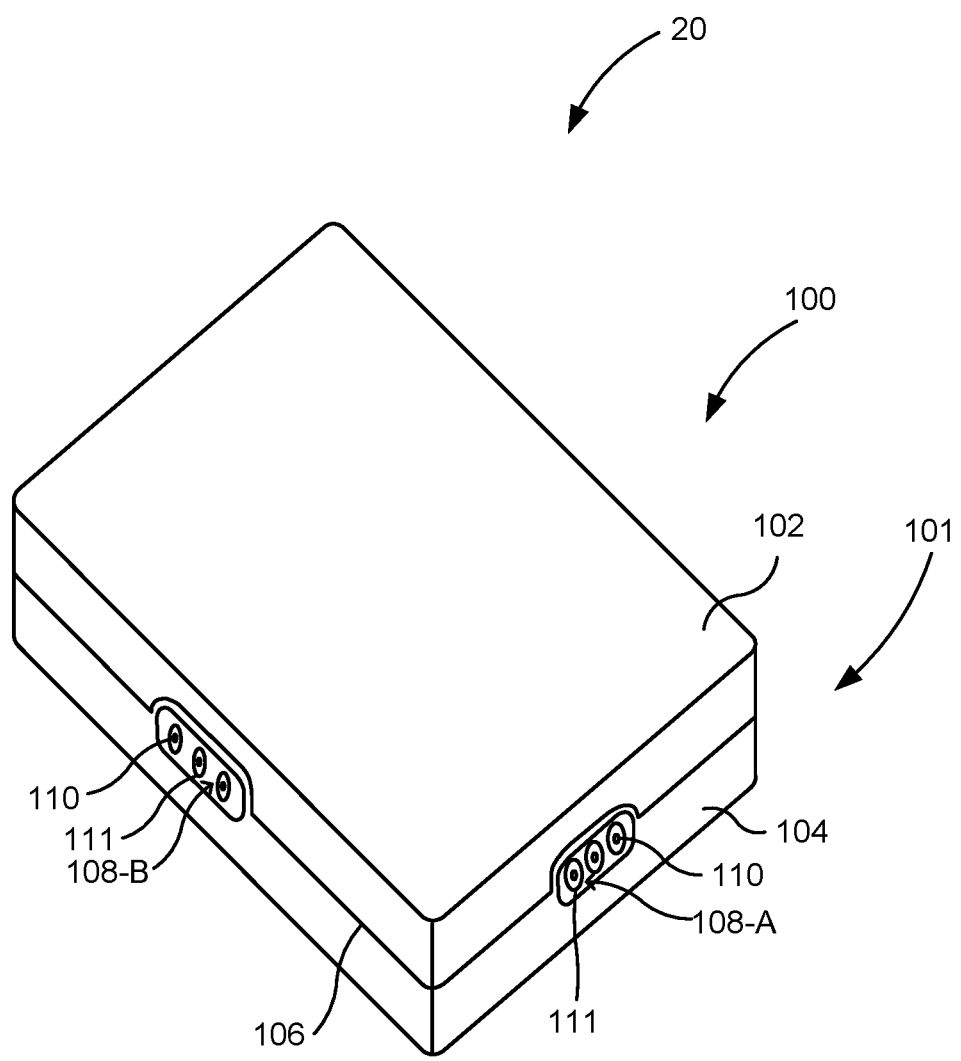
FIG. 2 is a perspective view of one embodiment of the system controller.

With reference now to FIG. 2, a perspective view of one embodiment of the system controller 20 is shown. The system controller 20 can be coupled to the blood pump 14, and can specifically be communicatively coupled to the blood pump 14. The system controller 20 can comprise a housing 100, that can define an internal volume. In some embodiments, the housing 100 can comprise a sealed housing 100 and/or a partially sealed housing 100. In some embodiments, the housing 100 can be sealed in a watertight manner so that water cannot enter into the internal volume, and/or in some embodiments, the housing 100 can be sealed in a non-airtight manner so as to allow gas to exit the housing 100, such as, for example, can occur after degassing of energy storage components, such as one or several batteries contained within the housing 100.

In some embodiments, the housing 100 can comprise a plurality of pieces 101 joined and/or sealed together to define the internal volume of the housing. As depicted in FIG. 2, these pieces 101 can include at least a first piece 102 and a second piece 104. These pieces can be connected by a sealed joint 106, also referred to herein as a joint 106 and/or as a seal 106. In some embodiments, the sealed joint 106 can comprise at least one of the weld, a gasket, an adhesive bond, a solvent bond, where the like. In some embodiments, these pieces 101, and/or the sealed joint 106 can be watertight, and in some embodiments, these pieces 101 and/or the sealed joint 106 can be watertight and non-airtight.

The housing 100 can comprise features configured to couple the controller 20 with other components of the mechanical circulatory support system 10. In some embodiments, these features can comprise one or several connector receptacles 108, also referred to herein as one or several receptacle connectors 108, located in a portion of the housing 100 and the connector receptacles 108 can each include one or several contacts 110, which one or several contacts can include, in some embodiments, at least one positive contact and at least one negative contact. In some embodiments, the one or several contacts can comprise an electrically conductive material such as a metal, a metal alloy, or the like. This can include, for example, a gold alloy, a silver alloy, an aluminum alloy, a steel alloy, a platinum alloy, and/or a palladium alloy.

In some embodiments, each of the contacts 110 can be surround by a dielectric 111, which dielectric 111 can be, for example, hydrophobic. In some embodiments, the dielectric 111 can interact with the mating connector of the connector insert to facilitate in expelling of any ingress such as, for example, water from between contacts, and this interaction between the dielectric 111 and the mating connector of the connector insert can prevent the return of any ingress after the contacts are mated. In some embodiments, the dielectric 111 and/or the contacts 110 can be designed to withstand initial arcing and/or to minimize initial arcing.

The connector receptacles 108 can be configured to receive one or several connector inserts to allow connection of the controller 20 with, for example, the blood pump 14 and/or the external power source 22. These connector receptacles 108 can include a first connector receptacle 108-A that can receive a connector insert coupling the controller 20 to, for example, the external power source 22 and a second connector receptacle 108-B that can receive a connector insert coupling, for example, the controller 20 to the blood pump 14 via, for example, the driveline 26. In some embodiments, the one or several connector receptacles 108 can be sealed so as to be watertight and/or can be sealed to be watertight and non-airtight. Similarly, in some embodiments, the connector insert for connecting with the connector receptacle can be sealed.

Figure 3:
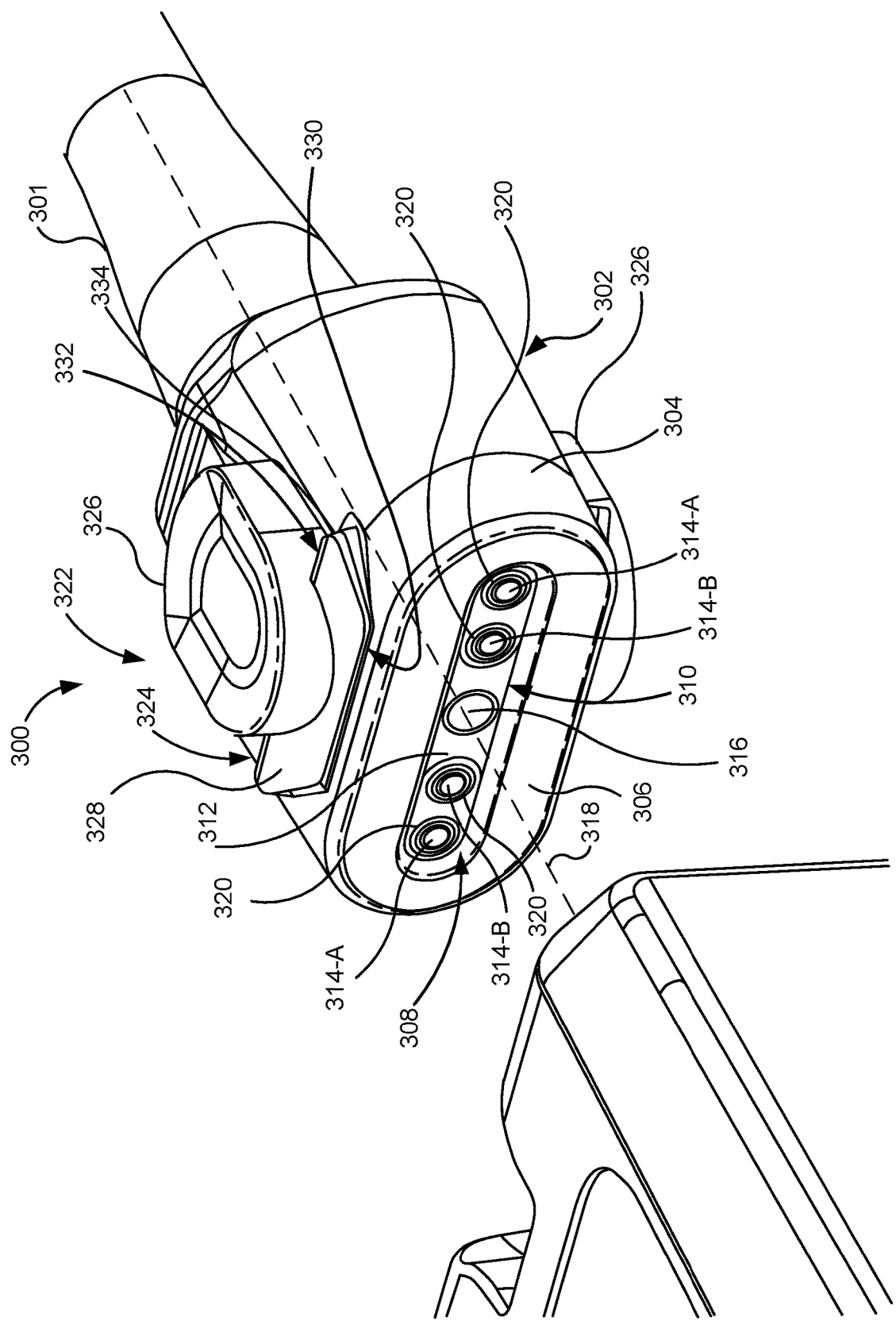
FIG. 3 is a perspective view of one embodiment of the connector insert.

With reference now to FIG. 3, a perspective view of one embodiment of the connector insert 300 is shown. The connector insert 300 can be located at an end of a tether 301 containing, for example, one or several wires, one or several light guides, or the like. The tether 301 can comprise the driveline 26, a cable connecting the extra power source 22 to the controller 20, or the like. The connector insert 300 comprises a body 302 having sides 304 and a front face 306, also referred to herein as the face 306. The body 302 of the connector insert 300 can be sealed, and specifically can be hermetically sealed and/or water sealed such that water cannot enter into the body. The connector insert 300 can comprise a plurality of insert contacts 308, also referred to herein as contacts 308, that can be located in a connector depression 310, and specifically can be located along a bottom 312 of the connector depression 310.

The contacts 308 can comprise a variety of shapes, sizes, arrangements, and/or types. In some embodiments, for example, the contacts 308 can comprise one or several electrical contacts 314, and/or one or several optical contacts 316. The electrical contacts 314 can include one or several first electrical contacts 314-A and one or several second electrical contacts 314-B. In the embodiment depicted in FIG. 3, the contacts 308 are linearly arranged. In this embodiment, the first electrical contacts 314-A are outside of the second electrical contacts 314-B, or in other words, the first electrical contacts 314-A are located farther from the midpoint of the linear arrangement of the contacts 308 than the second electrical contacts 314-B. In some embodiments, the first electrical contacts 314-A can have one of a positive or negative polarity, and the second electrical contacts 314-B can have the other of the positive or negative polarity.

In some embodiments, the contacts 308 can be arranged to allow the contacts 308 to mate with corresponding contacts of the connector receptacle when the connector insert 300 is in a single, predetermined orientation with respect to the connector receptacle, and/or when the connector insert 300 is in one of a set of predetermined orientations with respect to the connector receptacle. In some embodiments, for example, the body 302 of the connector insert 300 can comprise a shape allowing insertion of the connector insert 302. The connector receptacle in one orientation and/or in one of a set of orientations. In the embodiment of FIG. 3, the body 302, and specifically the face 306 of the body 302 has an elongate shape that, when paired with a connector receptacle having a similar elongate shape allows insertion of the connector insert 300 into the connector receptacle in one of two orientations. In some embodiments, the contacts 308 can be arranged to mate with corresponding contacts of the connector receptacle when the connector insert 300 is inserted into the connector receptacle regardless of the orientation of the connector insert 300 with respect to the connector receptacle. In the embodiment of FIG. 3, for example, when the first electrical contacts 314-A have one of the positive and negative polarity and the second electrical contacts 314-B have the other of the positive and negative polarity, the contacts 308 would properly mate with corresponding contacts of the connector receptacle regardless whether the connector insert 300 is in a first orientation shown in FIG. 3, or is in a second orientation in which the connector insert 300 is rotated 180° about a central axis 318 of the body 302.

The connector insert 300 can further comprise one or several seals 320. In some embodiments, the one or several seals 320 can extend around at least one of the contacts 308 of the connector insert 300, and specifically around at least one of the electrical contacts 314 of the connector insert 300. In the embodiment depicted in FIG. 3, each of the electrical contacts 314 can be encircled by a seal 320. In some embodiments, these seals 320 can be configured to mate with a portion of the connector receptacle so as to seal the electrical contacts 314 of the connector insert 300 and any mating contact of the connector receptacle from others of the electrical contacts 314 of the connector insert 300. Period. In some embodiments, this seal 320 can fluidly isolate the at least one of the electrical contacts 314 encircled by the seal 320 from others of the electrical contacts 314 that are not encircled by that seal when the connector insert 300 is received within the connector receptacle and when this seal 320 seals against the connector receptacle.

The connector insert 300 can include a locking mechanism 322. The locking mechanism 322 can maintain coupling between the connector insert 300 and the mating connector receptacle until the locking mechanism 322 is actuated to unlock the connector insert 300 to allow decoupling of the connector insert 300 and the connector receptacle. The locking mechanism 322 can comprise one or several locking features 324 and one or several control features 326, which control features 326 can comprise one or several buttons.

The locking features 324 can be sized, shaped, and/or configured to engage with all or portions of the connector receptacle to secure the connector insert 300 coupled to the connector receptacle. The locking features 324 can, and as depicted in FIG. 3, comprise a wedge-shaped member 328.

The wedge-shaped member 328 can extend from a front 330 of the wedge-shaped member 328 to a back 332 of the wedge-shaped member 328. In some embodiments, the back 332 of the wedge-shaped member 328 can be thicker than the front 330 of the wedge-shaped member 328, and the back 332 can comprise an abutting surface 334 which engages with features of the connector receptacle 402 shown in FIG. 4, below.

Figure 4:
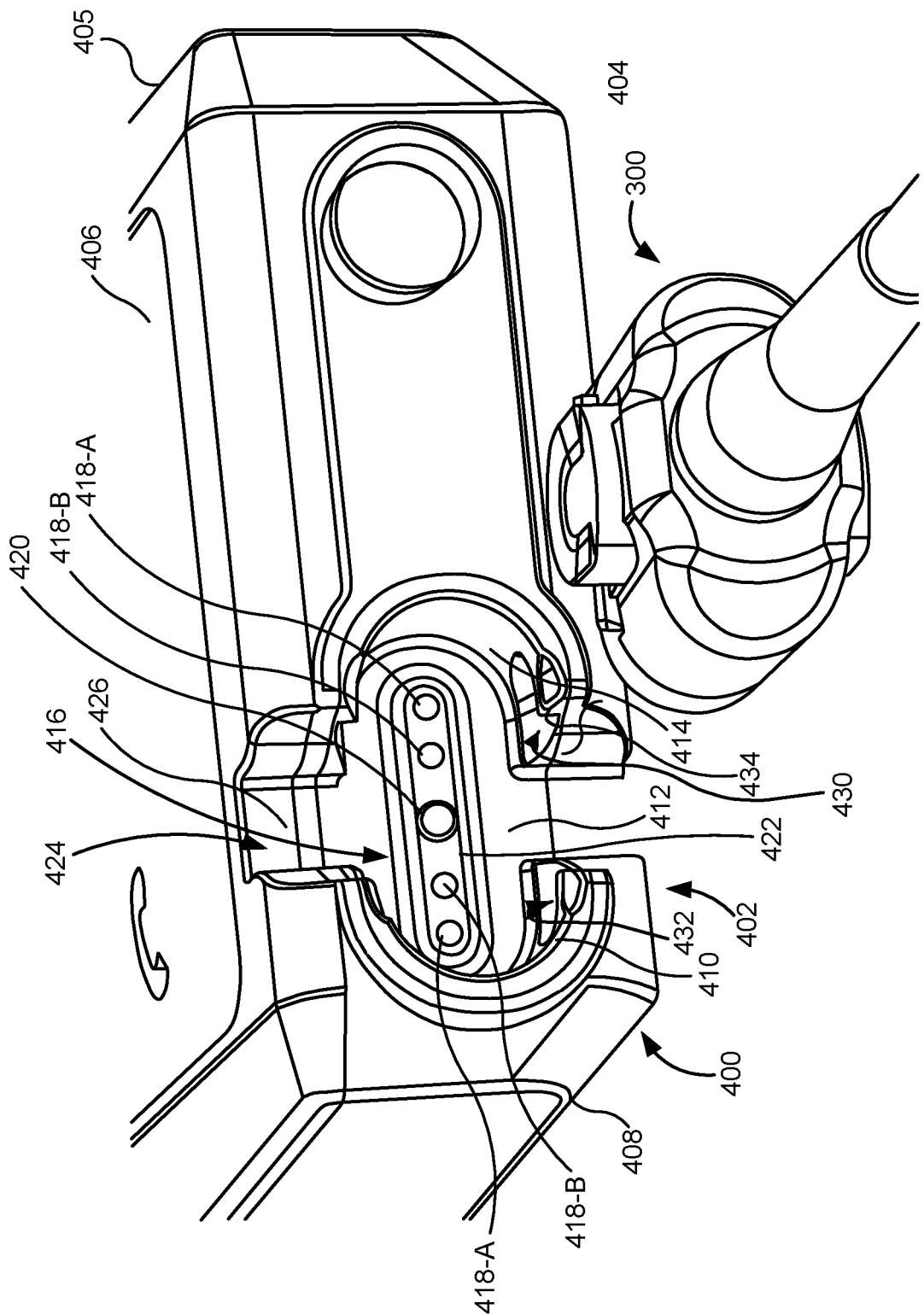
FIG. 4 is a perspective view of one embodiment of the connector insert and the connector receptacle.

With reference now FIG. 4, a perspective view of one embodiment of the connector insert 300 and medical device 400 including a connector receptacle 402, also referred to herein as a receptacle connector 402, is shown. The medical device 400 can be, for example, the implantable blood pump 14, the controller 20, or the power source 22. The medical device 400 can comprise a housing 404 having an external surface 405 defining an internal volume and having sides 406, 408, between which sides 406, 408, the connector receptacle 402 is located.

The connector receptacle 402 can comprise a top 410, a recessed base 412, and the sidewall 414 extending from the top 410 to the recessed base 412. In some embodiments, and as depicted in FIG. 4, the recessed base 412 is positioned at a depth below the top 410 of the connector receptacle 402. The connector receptacle 402 further includes a plurality of contacts 416 that can be arranged on the recessed base 412 of the connector receptacle 402. Some or all of the plurality of contacts 416 can be configured to engage, connect, and/or mate with some or all of the contacts 308 of the connector insert 300. In some embodiments, the plurality of contacts 416 can comprise a variety of shapes, sizes, arrangements, and/or types. In some embodiments, the contacts 416 can comprise one or several electrical contacts 418 and one or several optical contacts 420. In the embodiment depicted in FIG. 4, the plurality of contacts 416 comprise at least four electrical contacts 418 and an optical contact 420. The electrical contacts 418 can comprise one or several first electrical contacts 418-A and one or several second electrical contacts 418-B. In the embodiment depicted in FIG. 4, the electrical contacts 418 comprise two first electrical contacts 418-A, and two second electrical contacts 418-B.

In some embodiments, the contacts 416 can be arranged on a pedestal 422 that can be sized and shaped to be received within the connector depression 310 such that the contacts 416 can engage, connect, and/or mate with the contacts 308 of the connector insert 300. In the embodiment depicted in FIG. 4, the contacts 416 are linearly arranged, and specifically are arranged such that the first electrical contacts 418-A are outside of the second electrical contacts 418-B, or in other words, the first electrical contacts 418-A are located farther from the midpoint of the linear arrangement of the contacts 416, than the second electrical contacts 418-B. In some embodiments, the first electrical contacts 418-A can have one of a positive or negative polarity and the second electrical contacts 418-B can have the other of the positive or negative polarity. In some embodiments, for example, the electrical contacts 418 comprise two first electrical contacts 418-A both having a same one of a positive or negative polarity, and two second electrical contacts 418-B, both having a same other of the positive or negative polarity.

In some embodiments, the connector receptacle 402 can be sized and shaped to receive a connector insert 301 predetermined orientation, in one of a set of predetermined orientations, and/or in one of a finite number of positions or orientations. Thus, as seen in FIG. 4, the connector receptacle 402. As an elongate shape corresponding to the elongate shape of the connector insert 300 such that the connector insert 300 can be received in the connector receptacle 402 in one of two orientations. In some embodiments, the contacts 416 of the connector receptacle and the contacts 308 of the connector insert 300 are arranged for proper mating regardless of which of the finite number of orientations in which the connector insert 300 is received in the connector receptacle 402.

The connector receptacle 402 can comprise a drain feature 424, that can be configured to allow draining of a fluid, and/or of any fluid contained within the connector receptacle 402 when the connector insert 300 is inserted into the connector receptacle 402. In some embodiments, the drain feature can comprise a channel 426 that can extend from the top 410 to the recessed base 412 of the connector receptacle 402. In such an embodiment, the channel 426 can have a channel depth equal to a depth of the connector receptacle 402. In some embodiments, this channel 426 can be defined by the housing 404 of the medical device 400, and the channel 426 can extend through, for example, the sides 406, 408 of the housing 400.

The connector receptacle 402 can comprise one or several securement features 430 configured to engage with all or portions of the locking mechanism 322 to secure the coupling of the connector insert 300 to the connector receptacle 402. In some embodiments, these securement features 430 can be located in any desired portion of the connector receptacle 402 including, for example, at and/or in the housing 404 and specifically at or in the external surface 405 of the housing 404, at and/or in the top 410, at and/or in the recessed base 412, and/or at and/or in the sidewall 414.

In the embodiment of FIG. 4, the securement features 430 comprise depressions 432 located in the sidewall 414 of the connector receptacle 402. The depressions 432 comprise a stop wall 434 that is sized, shaped, and positioned to engage with the abutting surface 334 of the locking mechanism 322 when the connector insert 300 is received within the connector receptacle 402 and/or when the connector insert 300 and the connector receptacle 402 are coupled. In some embodiments in which the securement features 430 are located in the sidewall 414 of the connector insert 402, the stop wall 434 can be positioned at a desired distance from the recessed base 412, from the contacts 416, and/or from the pedestal 422 such that the locking mechanism 322 engages with the securement features 430 when the connector insert 300 reaches a desired depth of insertion in the connector receptacle 402 and/or when the connector insert 300 is fully inserted into the connector receptacle 402.

Figure 5:
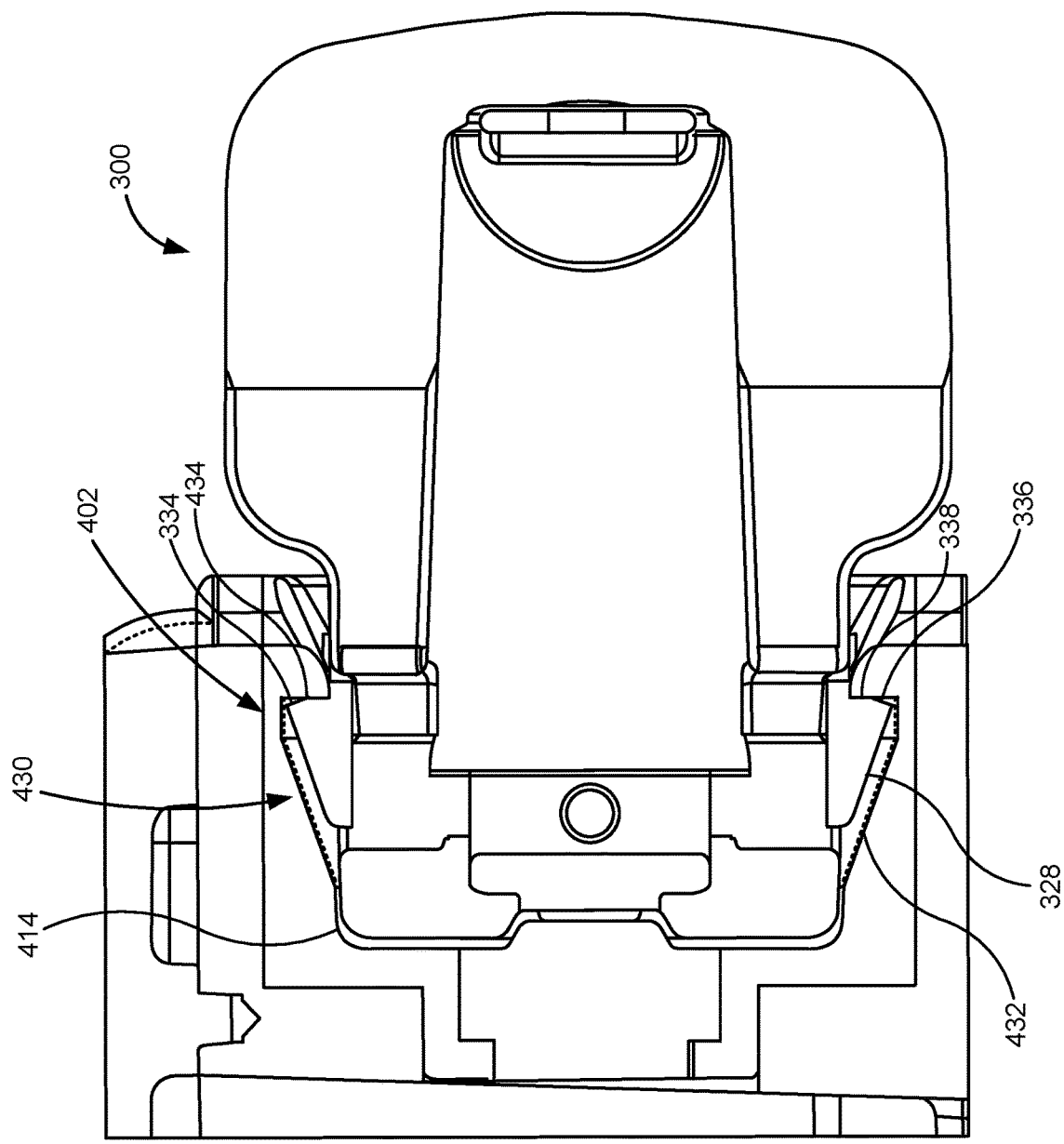
FIG. 5 is a section view of one embodiment of the connector insert and the connector receptacle.

With reference now to FIG. 5, a section view of the connector insert 300 coupled with the connector receptacle 402 is shown. As seen in FIG. 5, the locking mechanism 322, and specifically the abutting surface 334 has engaged with the securement features 430, and specifically with the stop wall 434. As seen in FIG. 5, the wedge-shaped member 328 of the locking mechanism 322 is received within the depressions 432 located in the sidewall 414 of the connector receptacle 402. The connector insert 300 is inserted into the connector receptacle 402 such that the connector insert 300 and the connector receptacle 402 are coupled, which coupling is secured by the mating interaction of the locking mechanism 322 with the securement features 430.

In some embodiments, and as shown in FIG. 5, the abutting surface 334 can comprise a first angled portion 336 and a second angled portion 338. In some embodiments, the first angled portion 336 can have a first orientation and the second angled portion 338 can have a second orientation. In some embodiments, the first orientation of the first angled portion 336 can be selected to allow engagement of the abutting surface 334 as the connector insert 300 is inserted into the connector receptacle 402 and before the complete insertion of the connector insert 300 into the connector receptacle, and in some embodiments, the second orientation of the second angled portion 338 can be selected to maximize locking when the connector insert 300 is fully inserted into the connector receptacle 402 and/or has achieved at least a desired level of insertion into the connector receptacle 402. The inclusion of the first and second angled portions 336, 338 facilitate successful coupling of the connector insert 300 and the connector receptacle 402, particularly in light of variations in size of one or both of the connector insert 300 and the connector receptacle 402.

Figure 6:
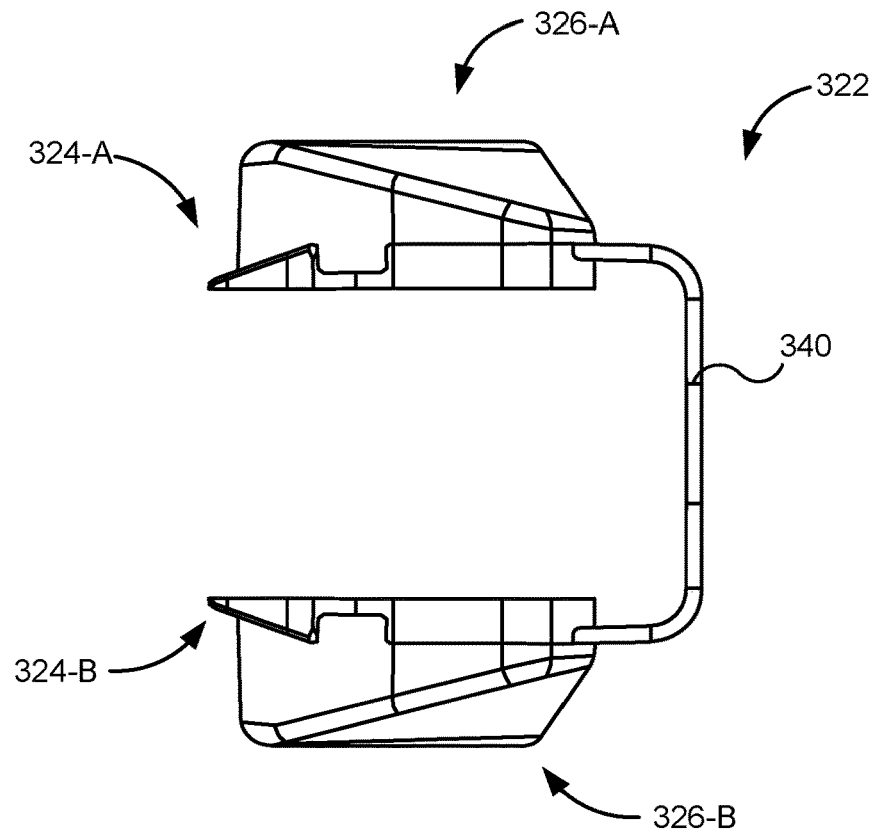
FIG. 6 is a side view of one embodiment of a locking mechanism.
Figure 7:
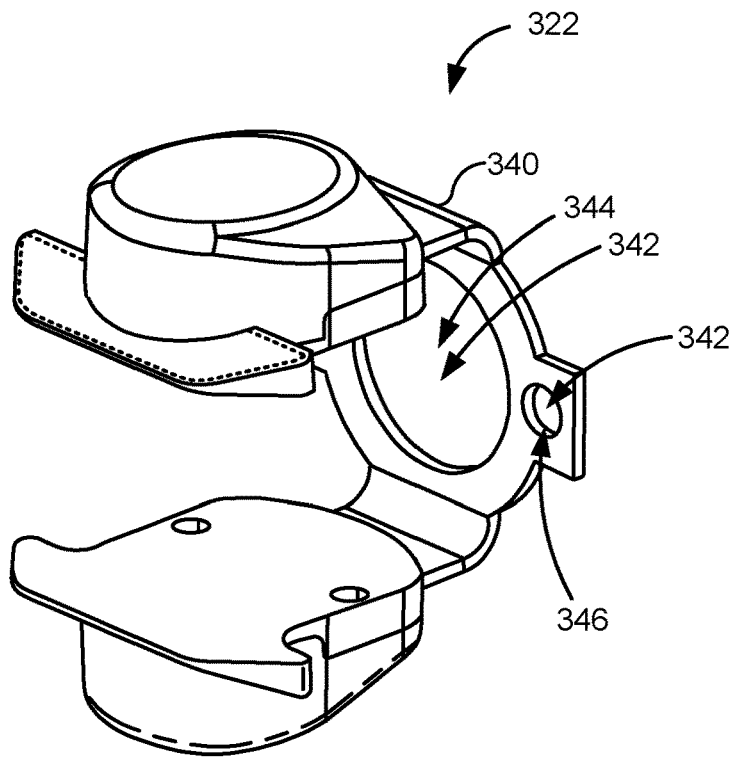
FIG. 7 is a perspective view of one embodiment of the locking mechanism.

The locking mechanism 322, can comprise a variety of shapes, sizes, and features. FIGS. 6 through 7 show embodiments of the locking mechanism 322. The locking mechanism 322 includes the locking features 324. In the depicted embodiments, the locking features 324 include a first locking feature 324-A and a second locking feature 324-B. In some embodiments, the first locking feature 324-A can be configured to engage a first portion of the connector receptacle 402 and the second locking feature 324-B can be configured to engage a second portion of the connector receptacle 402.

The locking mechanism 322 further includes control features 326, and specifically includes a first control feature 326-A and a second control feature 326-B. The first control feature 326-A can be coupled to the first locking feature 324-A such that manipulation of the first control feature 326-A affects the position of the first locking feature 324-A and the ability of the first locking feature 324-A to engage with the securement features 430 of the connector receptacle. The second control feature 326-B can be coupled to the second locking feature 324-B such that manipulation of the second control feature 326-B affects the position of the second locking feature 324-B and the ability of the second locking feature 324-B to engage with the securement features 430 of the connector receptacle.

The first and second locking features 324-A, 324-B and the first and second control features 326-A, 326-B are coupled via a connection member 340. The connection member 340 can comprise a variety of shapes and sizes and can be made from a variety of materials. In some embodiments, the connection member 340 can be at least partially flexible to allow movement of the first and second locking features 324-A, 324-B from a locked position in which the first and second locking features 324-A, 324-B can engage with securement features 430 to a disengaged position in which the first and second locking features 324-A, 324-B are retracted from engagement with the securement features 430.

In some embodiments, the locking mechanism 322 can be configured such that the locking mechanism 322 automatically locks the connector insert 300 in the connector receptacle 402 when the connector insert 300 is inserted into the connector receptacle 402. In some embodiments, this automatic locking can occur due to the connection member 340 biasing the locking features 324 towards a locked position. In some embodiments, the locking mechanism can be disengaged to allow the selective decoupling of the connector insert 300 from the connector receptacle 402 via the simultaneous manipulation of the control features 326. In the embodiment depicted herein, the unlocking of the locking mechanism 322 can occur via the simultaneous manipulation of both the first and second control features 326-A, 326-B.

As seen in FIG. 7, in some embodiments, the connection member 340 can define one or several apertures 342. These apertures 342 can comprise a central aperture 344 and a securement aperture 346. In some embodiments, In some embodiments the central aperture 344 can allow passing of one or several components through the connection member 340. These components can include, for example, one or several wires, cables, or the like. The securement aperture 346, and in some embodiments, a plurality of securement apertures 346 can facilitate in coupling the connection member 340, and thus the locking mechanism 322 to the connector insert 300.

In some embodiments, the connector insert 300 and the connector receptacle 402 can be used to couple portions of the mechanical circulatory support system 10. This can include inserting the connector insert 300 into the connector receptacle 402, which connector receptacle can be located in the housing 404 of the medical device 400. As discussed above, this connector receptacle can include contacts 418 that can mate with contacts 308 of the connector insert 300 when the connector insert 300 is fully received within the connector receptacle 402. As the connector insert 300 is inserted into the connector receptacle 402, fluid can be drained from the connector receptacle 402 via the drain feature 424 which can comprise the channel 426 extending through the connector receptacle 402. The contacts 308 of the connector insert 300 can be mated with the contacts 416 of the connector receptacle 402 when the connector insert 300 is fully inserted and/or received within the connector receptacle. In some embodiments, a seal 320 extending around at least one of the contacts 308, 416, and specifically extending around at least or receptacle as the connector insert advances into the connector receptacle; connector insert 300 and the connector receptacle to seal the at least one of the contacts 308, 416, around which the seal 320 extends when the connector insert 300 is received within the connector receptacle 402. This seal can fluidly isolate the at least one contact 308, 416, around which the seal 320 extends from others of the contacts 308, 416 of the connector insert 300 and/or of the connector receptacle 402 when the seal 320 is compressed between the connector insert 300 and the connector receptacle 402.

Figure 8:
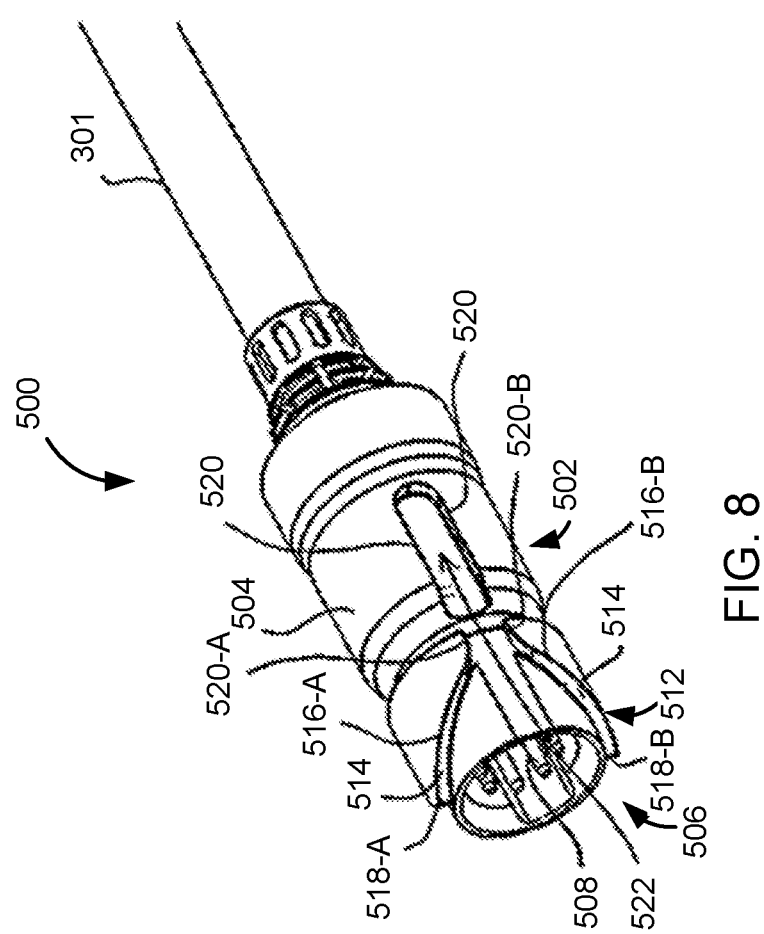
FIG. 8 is a perspective view of another embodiment of a connector insert.

With reference now to FIG. 8, a perspective view of another embodiment of a connector insert 500 is shown. The connector insert 500 can comprise a plurality of insert contacts 508, also referred to herein as contacts 508. The connector insert 500 can be located at an end of the tether 301 containing, for example, one or several wires, one or several light guides, or the like. The tether 301 can comprise the driveline 26, a cable connecting the extra power source 22 to the controller 20, or the like. The connector insert 500 comprises a body 502 having sides 504 and a front 506. The body 502 of the connector insert 500 can be sealed, and specifically can be hermetically sealed and/or embodiments, the insert contacts 508 can comprise a plurality of pins which can be arranged in any desired layout and can, in some embodiments, be arranged in a circle or ring.

The connector insert 500 can comprise at least one mating feature 512, which can interact with orientation features of the connector receptacle to bring the connector insert 500 to a desired orientation, and/or alignment with respect to the connector receptacle. In some embodiments, the mating feature 512 can engage with the orientation features of the connector receptacle to bring the connector insert 500 to desired orientation and/or alignment with respect to the connector receptacle when or while the connector insert 500 is inserted into the connector receptacle. In some embodiments, for example, the mating feature 512 can interact with the orientation features of the connector receptacle such that the further the connector insert 500 is inserted into the connector receptacle, the closer the actual alignment, and/or orientation of the connector insert 500 is to the desired orientation, and/or alignment.

In some embodiments, the mating feature 512 can comprise one or several cam surfaces 514 that can be configured to engage the orientation, feature, which can be a following surface, to bias the connector insert 500 to a desired alignment with respect to the connector receptacle when the connector insert 500 is inserted into the connector receptacle. Specifically, in some embodiments, the following surface of the connector receptacle can slide along or across all or portions of the cam surfaces 514. The cam surfaces 514 can extend and/or wrap around all or portions of the connector insert 500.

In some embodiments, a cam surface 514 can comprise a pair of inclined planes 516, each of which can slope from a point 518 to a wall 520 such that each of the pair of inclined planes 516 terminates at a wall 520 and/or at a follower receptacle 522. In some embodiments, walls 520 can define the follower receptacle 522, also referred to herein as the key slot 522. The connector receptacle 522 can receive the orientation feature of the connector receptacle when the desired alignment, and/or orientation, the connector insert 500 with respect, the connector receptacle is attained. In some embodiments, the inclined planes 516 can comprise a first inclined plane 516-A extending from a first point 518-A to a first wall 520-A, and the second inclined plane 516-B extending from a second point 518-B to a second wall 518-B. In some embodiments, the first inclined plane 518-A can have a negative slope and the second inclined plane 516-B can have a positive slope. In some embodiments, the first and second inclined planes 516-A, 516-B can be shaped having a funnel mouth between the first and second points 518-A, 518-B and the stem at the follower receptacle 522. In some embodiments, the pair of inclined planes 516 can comprise a first pair of inclined planes 516 arranged in a funnel shape and/or extending or wrapping around a first portion of the connector insert 500 and a second pair of inclined planes 516 arranged in a funnel shape and/or extending or wrapping around a second portion of the connector insert 500. In some embodiments, one of the inclined planes in the first pair of inclined planes intersects one of the inclined planes of the second pair of inclined planes at the first point 518-A, and the other of the inclined planes in the first pair of inclined planes intersects the other of the inclined planes of the second pair of inclined planes at the second point 518-B.

In some embodiments, the cam surface 514 can be configured to cause the connector insert 500 to rotate with respect to the connector receptacle when the connector insert 500 is inserted into the connector receptacle. In some embodiments, the cam surface 514 and the key slot 522 can be sized, shaped, and/or positioned such that the rotation of the connector insert 500 with respect to the connector receptacle stops and/or such that the orientation feature is received or partially received within the key slot before any of the plurality of insert contacts 508 mates with, engages with, and/or contacts any of the contacts of the connector receptacle.

Figure 9:
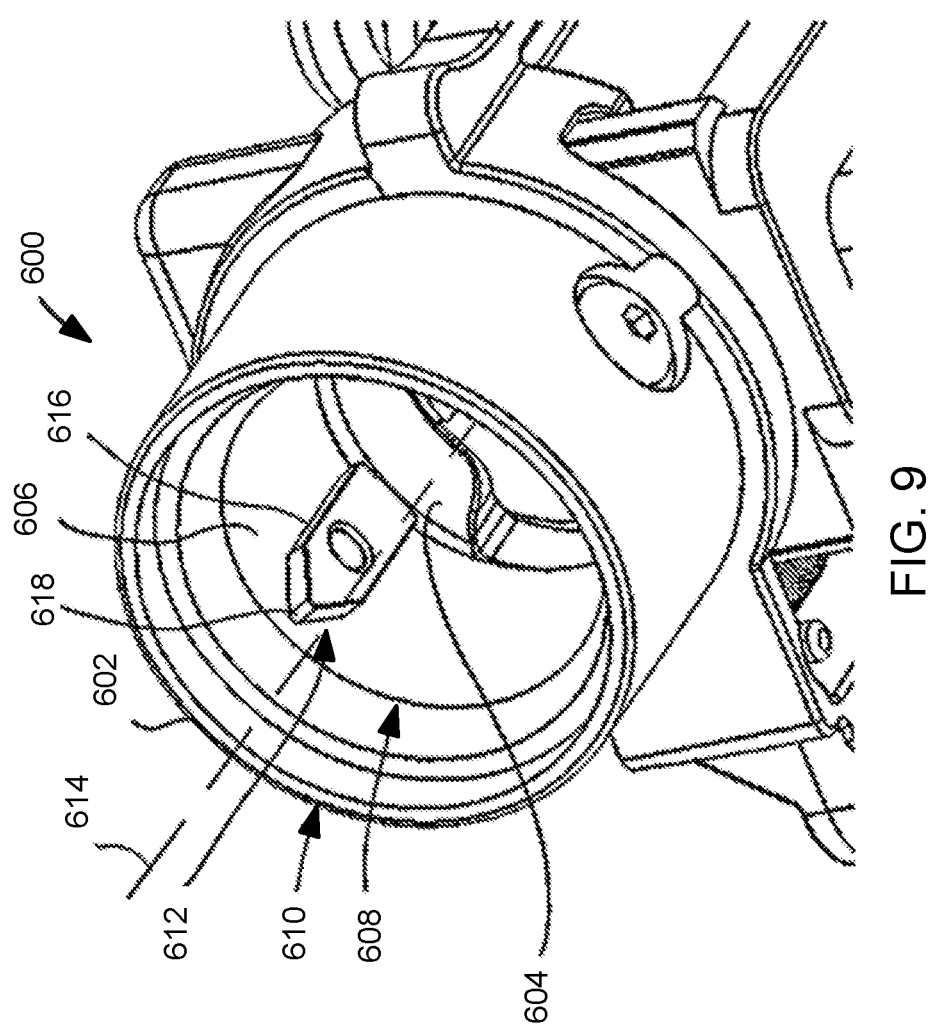
FIG. 9 is a perspective view of another embodiment of the connector receptacle.

With reference now to FIG. 9, a perspective view of one embodiment of a receptacle connector 600, also referred to herein as a connector receptacle 600, is shown. The connector receptacle 600 can be included in medical device 400 in the place of receptacle connector 402, and specifically can be positioned between sides 406, 408 of housing 404 of medical device 400. The connector receptacle 600 can comprise a top 602, a recessed bottom 604, and a side 606, also referred to herein as a wall 606 or as a sidewall 606, connecting the top 602 and the bottom 604. In some embodiments, the sidewall 606 can extend from the top 602, which can be located at the surface 405 of the medical device 400 to the bottom 604 of the receptacle connector 600. The connector receptacle 600, and specifically the wall 606 and the bottom 604 of the connector receptacle 600 can define a receptacle volume 608 that can be accessed via an opening 610 defined by the top 602 of the connector receptacle 600.

The connector receptacle 600 can include an orientation feature 612, also referred to herein as a following surface 612 or following feature 612, that can be configured to engage with the at least one mating feature 512 of the connector insert 502 of the connector insert to a desired alignment with respect, the connector receptacle 600 while the connector insert 500 is inserted into the connector receptacle 600. In some embodiments, the following surface 612 can radially inwardly extend towards a central axis 614 of the connector receptacle 600.

In the embodiment depicted in FIG. 9, the following surface 612 comprises a key 616, and specifically comprises a pointed key having a pointed tip 618 directed towards the opening 610 of the receptacle volume 608. In some embodiments, the key 616, and specifically the pointed tip 618 can be configured to engage with the cam surface 514, and specifically can be configured to slide along and/or across the cam surface 514, and the key can be configured to be received within the key slot 522 of the connector insert 500 when the connector insert is at a desired alignment with respect to the connector receptacle 600 and when the connector insert is fully received within the receptacle volume 608 of the connector receptacle 600. In some embodiments, the key 616 can comprise a first key located on a first portion of the wall 606 and a second key located on the second portion of the wall 606. In some embodiments, the first key and the second key are located on opposite sides of the wall 606 across the receptacle volume 608.

Figure 10:
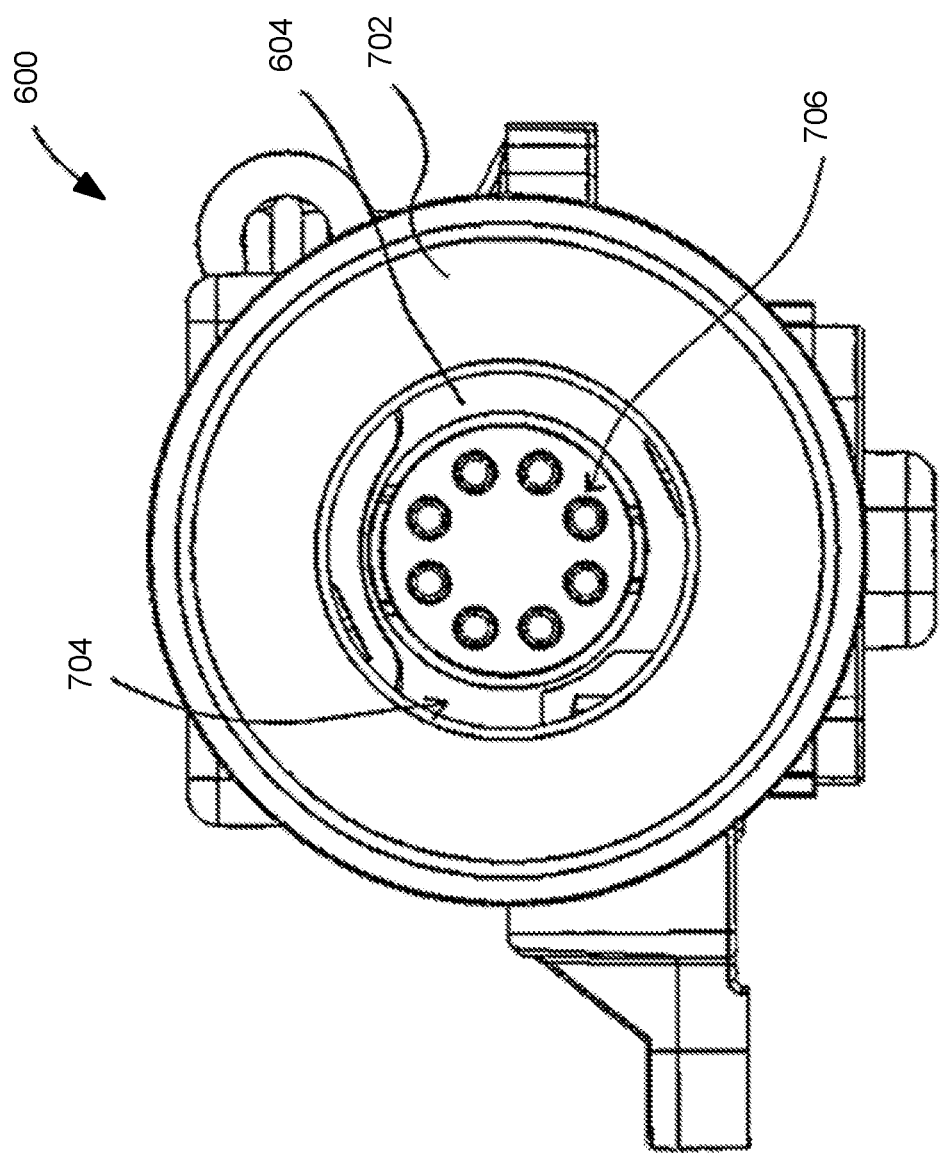
FIG. 10 is a front view of one embodiment of the connector receptacle.

With reference now to FIG. 10, a front view of one embodiment of the connector receptacle 600 is shown. The connector receptacle 600 can include a seal 702 that can be configured to sealingly mate with at least a portion of the connector insert 500. When the connector insert is received within the connector receptacle 600. The seal 702 can comprise a variety of shapes and sizes and can be made from a variety of materials. In some embodiments, the seal 702 can comprise an elastic and/or compliant material. The compliance allows the connector insert 500 to enter into the connector receptacle 600 and seals around the connector insert 500. As shown FIG. 10, the seal 702 can comprise an annular member having a central opening 704 through which the connector insert 500 can be inserted into the connector receptacle 600. The seal 702 can, in some embodiments, be positioned at the opening 610 of the receptacle volume 608.

The connector receptacle 600 can further comprise a plurality of contacts 706 configured for mating with corresponding contacts 508 of the connector insert 500 when the connector insert is coupled with the connector receptacle 600. In some embodiments, the plurality of contacts 706 can be located at or on the bottom 604 of the connector receptacle 600. The contacts 706 can be arranged in a desired pattern including, for example, in a ring as depicted in FIG. 10.

In some embodiments, the connector insert 500 and the connector receptacle 600 can be used to couple portions of the mechanical circulatory support system 10. This can include contacting the mating feature 512 of the connector insert 500 to the orientation feature 612 of the connector receptacle 600. In some embodiments, when the mating feature 512 of the connector insert 500 is first contacted to the orientation feature 612. The connector insert 500 can then be advanced into the connector receptacle 600, and specifically into the receptacle volume 608 of the connector receptacle 600. In some embodiments, as the connector insert 500 is being advanced into the connector receptacle 600, the seal 702 can seal on and/or around the connector insert 500. In some embodiments, the connector insert 500 can have a first orientation with respect to the connector receptacle 600 when the connector insert 500 is first being advanced into the connector receptacle 600.

As the connector insert 500 is advanced into the connector receptacle 600, the connector insert 500 can be reoriented from the first orientation to a second orientation in which they connector insert 500 is in the desired orientation, and/or alignment with respect to the receptacle connector, 600 via interaction between the orientation feature 612 of the connector receptacle 600 and the mating feature 512 of the connector insert 500. In some embodiments, this interaction between the orientation feature 612 of the connector receptacle 600 and the mating feature 512 of the connector insert 500 can automatically reoriented the connector insert 500 with respect to the connector receptacle 600 and the connector insert 500 advances into the connector receptacle 600. After the connector insert 500 is brought to the desired alignment, and/or orientation with respect to the connector receptacle 600, the orientation feature 612, which can be the key 616 is received within the key slot 500 to the connector insert and the electrical contacts 508 of the connector insert 500, are mated, engaged, and/or connected with the electrical contacts 706 of the connector receptacle 600.

With reference to FIGS. 11 through 21, embodiments of a connector system are shown. In some embodiments, the connector system can include features that can facilitate and ease coupling and/or connecting of connectors in the connector system. In some embodiments, this can include one or several features that facilitate in alignment of the connectors with respect to each other and the selective securing of the connectors in a coupled configuration. The one or several features that facilitate alignment can comprise features that can automatically bring the connectors to a desired alignment when the connectors of the connector system are coupled and/or connected. This can include, for example, features that change the orientation of one of the connectors with respect to the other one of the connectors to bring the connectors to a desired alignment and/or relative orientation as the connectors are connected and/or coupled. In one particular embodiment, these features can include one or several cam and following features that interact to change the relative orientation and/or alignment of the connectors with respect to each other as one of the connectors is inserted into the other of the connectors.

In some embodiments, the connectors of the connector system can be selectively secured to each other when coupled and/or connected. In some embodiments, this selecting securement can be achieved via one or several features that lock, and specifically that automatically lock the connectors together when the connectors are coupled. These features can include, for example, one or several blocking features that can receive a pin when the connectors are coupled. The blocking feature can prevent the decoupling and/or disconnection of the connectors. As the connectors are coupled and/or connected, the pin can be moved to mate with the blocking feature by a biasing member.

Figure 11:
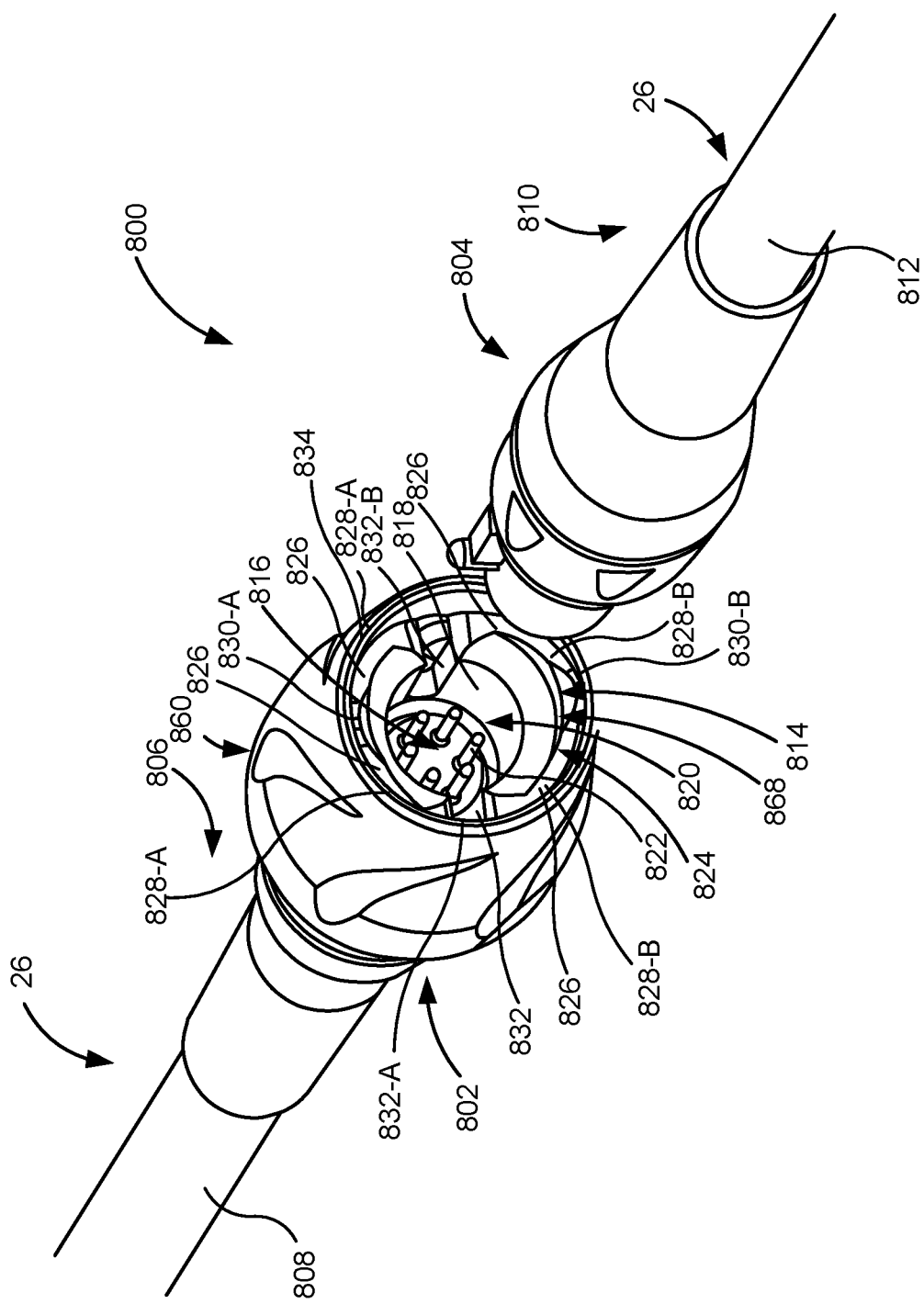
FIG. 11 is a perspective view of a connector system.
Figure 12:
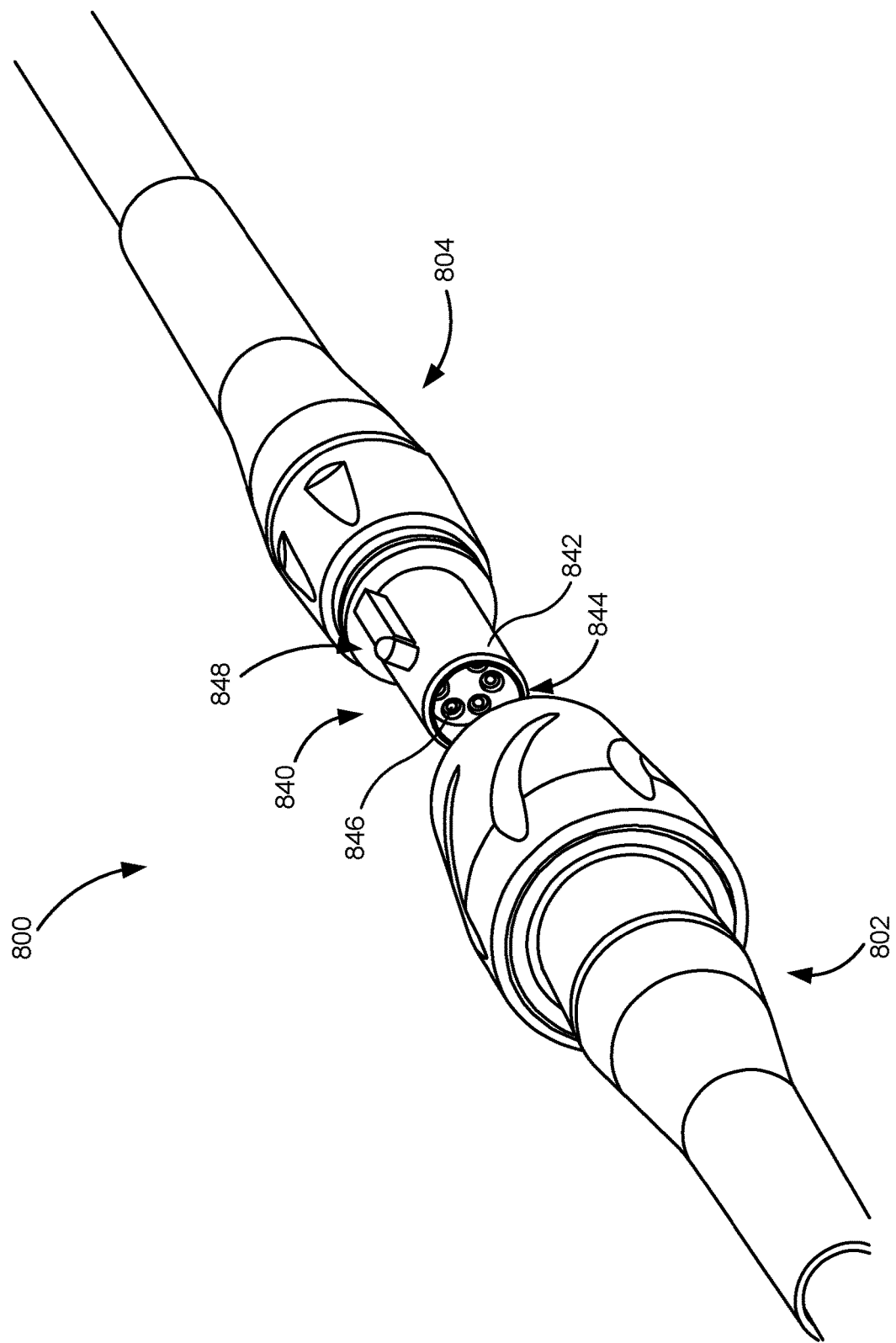
FIG. 12 is an additional perspective view of the connector system.

With reference now to FIGS. 11 and 12, perspective views of one embodiment of a connector system 800 is shown. The connector system 800 can comprise a connector receptacle 802 and a connector insert 804. One or both of the connector receptacle 802 and connector insert 804 can be located on or in a medical device such as, for example, in or on a component of the mechanical circulatory support system 10 including, for example, the implantable blood pump 14, the system controller 20, one or both of the external power sources 22, and/or the driveline. In the embodiment shown in FIG. 11, each of the connector receptacle 802 and the connector insert 804 are located in the driveline 26, which driveline is a two-piece driveline 26. Specifically, the connector receptacle 802 is located at an end 806 of a first piece 808 of the two-piece driveline 26 and the connector insert 804 is located at an end 810 of a second piece 812 of the two piece driveline 26. In some embodiments, the system controller 20 can be coupled to the implantable blood pump 14 via the driveline 26, which can be the two-piece driveline 26 shown in FIG. 11, and the connector system 800 can connect the first and second pieces 808, 812 of the driveline 26.

The connector receptacle 802 can comprise a top 814, also referred to herein as an end 814, a recessed bottom 816, and a side 818, also referred to herein as a wall 818 or as a sidewall 818, connecting the top 814 and the bottom 816. In some embodiments, the sidewall 818 can extend from the top 814 to the bottom 816 of the receptacle connector 802. The connector receptacle 802, and specifically the wall 818 and the bottom 816 of the connector receptacle 802 can define a receptacle volume 820 that can be accessed via an opening defined by the top 814 of the connector receptacle 802.

Although depicted as at an end of a piece of the driveline 26, the connector receptacle 802 can be located at an end of the tether 301 containing, for example, one or several wires, one or several light guides, or the like. The tether 301 can comprise the driveline 26, a cable connecting the extra power source 22 to the controller 20, or the like.

The connector receptacle 802 can comprise a plurality of contacts 822. In some, the contacts 822 can comprise a plurality of pins which can be arranged in any desired layout and can, in some embodiments, be arranged in a circle or ring. The contacts 822 can be configured for mating with corresponding contacts of the connector insert 804 when the connector insert 804 is coupled with the connector receptacle 802. In some embodiments, the plurality of contacts 822 can be located at or on the bottom 816 of the connector receptacle 802. The contacts 822 can be arranged in a desired pattern including, for example, in a ring as depicted in FIG. 11.

The connector receptacle can comprise at least one mating feature 824, which can interact with orientation features of the connector insert 804 to bring the connector insert 804 to a desired orientation, and/or alignment with respect to the connector receptacle 802. In some embodiments, the mating feature 824 can engage with the orientation features of the connector insert 804 to bring the connector insert 804 to desired orientation and/or alignment with respect to the connector receptacle 802 when or while the connector insert 804 is inserted into the connector receptacle 802. In some embodiments, for example, the mating feature 824 can interact with the orientation features of the connector insert 804 such that the further the connector insert 804 is inserted into the connector receptacle 802, the closer the actual alignment, and/or orientation of the connector insert 804 is to the desired orientation, and/or alignment.

In some embodiments, the mating feature 824 can comprise one or several cam surfaces 826 that can be configured to engage the orientation, feature, which can be a following surface, to bias the connector insert 804 to a desired alignment with respect to the connector receptacle 802 when the connector insert 804 is inserted into the connector receptacle 802. Specifically, in some embodiments, the following surface of the connector insert 804 can slide along or across all or portions of the cam surfaces 826. The cam surfaces 826 can extend and/or wrap around all or portions of the connector receptacle 802, and specifically around all or portions of the end 814

In some embodiments, a cam surface 826 can comprise a pair of inclined planes 828, each of which can slope from a point 830 to a wall 832 such that each of the pair of inclined planes 828 terminates at a wall 832 and/or at a follower receptacle 834. In some embodiments, walls 832 can define the follower receptacle 834, also referred to herein as the key slot 834. The connector receptacle 834 can receive the orientation feature of the connector insert 804 when the desired alignment, and/or orientation, of the connector insert 804 with respect, the connector receptacle 802 is attained. In some embodiments, the inclined planes 828 can comprise a first inclined plane 828-A extending from a first point 830-A to a first wall 832-A, and the second inclined plane 828-B extending from a second point 830-B to a second wall 832-B. In some embodiments, the first inclined plane 828-A can have a negative slope and the second inclined plane 828-B can have a positive slope. In some embodiments, the first and second inclined planes 828-A, 828-B can be shaped having a funnel mouth between the first and second points 830-A, 830-B and the stem at the follower receptacle 834. In some embodiments, the pair of inclined planes 828 can comprise a first pair of inclined planes 828 arranged in a funnel shape and/or extending or wrapping around a first portion of the connector receptacle 802 and a second pair of inclined planes 828 arranged in a funnel shape and/or extending or wrapping around a second portion of the connector receptacle 802. In some embodiments, one of the inclined planes 828 in the first pair of inclined planes 828 intersects one of the inclined planes 828 of the second pair of inclined planes 828 at the first point 830-A, and the other of the inclined planes 828 in the first pair of inclined planes 828 intersects the other of the inclined planes 828 of the second pair of inclined planes 828 at the second point 830-B.

In some embodiments, the cam surface 826 can be configured to cause the connector insert 804 to rotate with respect to the connector receptacle 802 when the connector insert 804 is inserted into the connector receptacle 802. In some embodiments, the cam surface 826 and the key slot 834 can be sized, shaped, and/or positioned such that the rotation of the connector insert 802 with respect to the connector receptacle 804 stops and/or such that the orientation feature is received or partially received within the key slot 834 before any of the plurality of contacts 822 mates with, engages with, and/or contacts any of the contacts of the connector insert 804.

Although depicted as at an end of a piece of the driveline 26, the connector insert 804 can be located at an end of the tether 301 containing, for example, one or several wires, one or several light guides, or the like. The tether 301 can comprise the driveline 26, a cable connecting the extra power source 22 to the controller 20, or the like. The connector insert 804 comprises a body 840 having sides 842, also referred to as exterior sides 842, and a front 844. The body 840 of the connector insert 804 can be sealed, and specifically can be hermetically sealed and/or embodiments, the connector insert 804 can include insert contacts 846 which can be arranged in any desired layout and can, in some embodiments, be arranged in a circle or ring.

The connector insert 804 can include an orientation feature 848, also referred to herein as a following surface 848 or following feature 848, that can be configured to engage with the at least one mating feature 824 of the connector receptacle 802 to rotate the connector insert 804 to a desired alignment with respect to the connector receptacle 600 while the connector 804 is inserted into the connector receptacle 802. In some embodiments, the following surface 848 can extend from the side 842 of the body 840 of the connector insert 804, and in some embodiments, the following surface 848 can radially outwardly extend from the side 842 of the body 840 of the connector insert 804.

Figure 13:
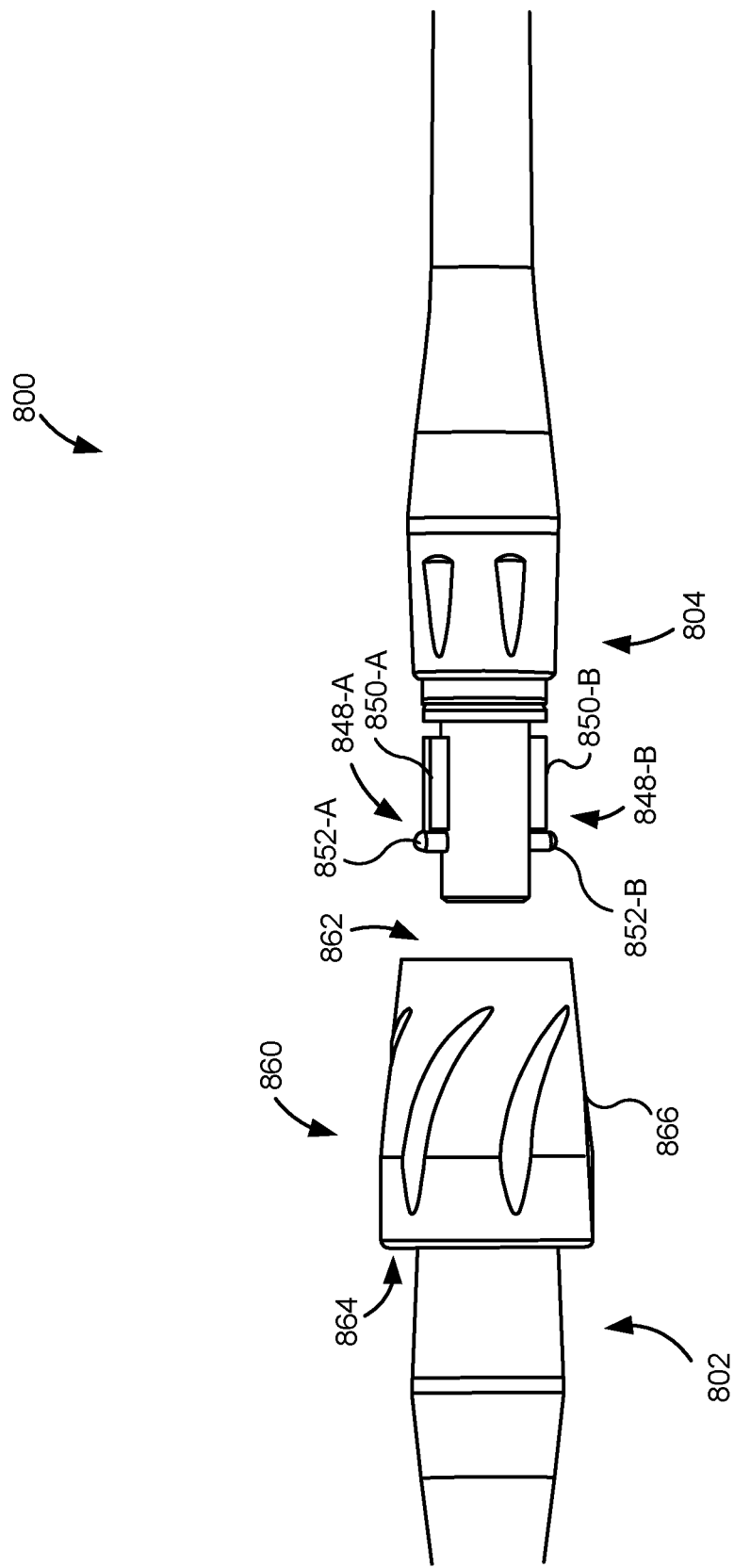
FIG. 13 is a side view of the connector system in a disconnected configuration.

The following surface 848 comprises a key 850 and/or a cylindrical member such as a circular cylindrical member 852, such as a pin. In some embodiments, the circular cylindrical member 852 can be configured to engage with the cam surface 826, and specifically can be configured to slide along and/or across the cam surface 826, and the circular cylindrical member 852 and the key 850 can be configured to be received within the key slot 834 of the connector receptacle 802 when the connector insert 804 is at a desired alignment with respect to the connector receptacle 802 and when the connector insert 804 is fully received within the connector receptacle 802. As seen in FIG. 13, in some embodiments, the following surface 848 can comprise a first following surface 848-A and a second following surface 848-B. In such an embodiment, the first following surface 848-A can comprise a first key 850-A and a first circular cylindrical member 852-B and the second following surface 848-B can comprise a second key 850-B and a second circular cylindrical member 852-B. In some embodiments, the first and second following surfaces 848-A, 848-B are located on opposite sides of the body 840 of the connector insert 804.

The connector system 800 can comprise a locking member 860. The locking member 860 can include a front 862, a back 864, and a body 866 extending from the front 862 to the back 864. As depicted in FIGS. 11 through 13, the locking member 860 extends at least partially around the connector receptacle 802, and specifically, the locking member 860 can include a channel 868 in which the connector receptacle 802 is at least partially received such that the body 866 of the locking member 860 extends around at least a portion of the connector receptacle 802. In some embodiments, the locking member 860 can be rotatable and/or can rotate about the connector receptacle 802.

The locking member 860 can engage and/or selectively engage with all or portions of the connector insert 804 to retain coupling between the connector receptacle 802 and the connector insert 804. In some embodiments, the locking member 860 selectively engages with a portion of the following surface 848, and specifically with the circular cylindrical member 852 to retain at least a portion of the following surface 848 within the follower receptacle 834 and/or to retain coupling between the connector receptacle 802 and the connector insert 804.

Figure 14:
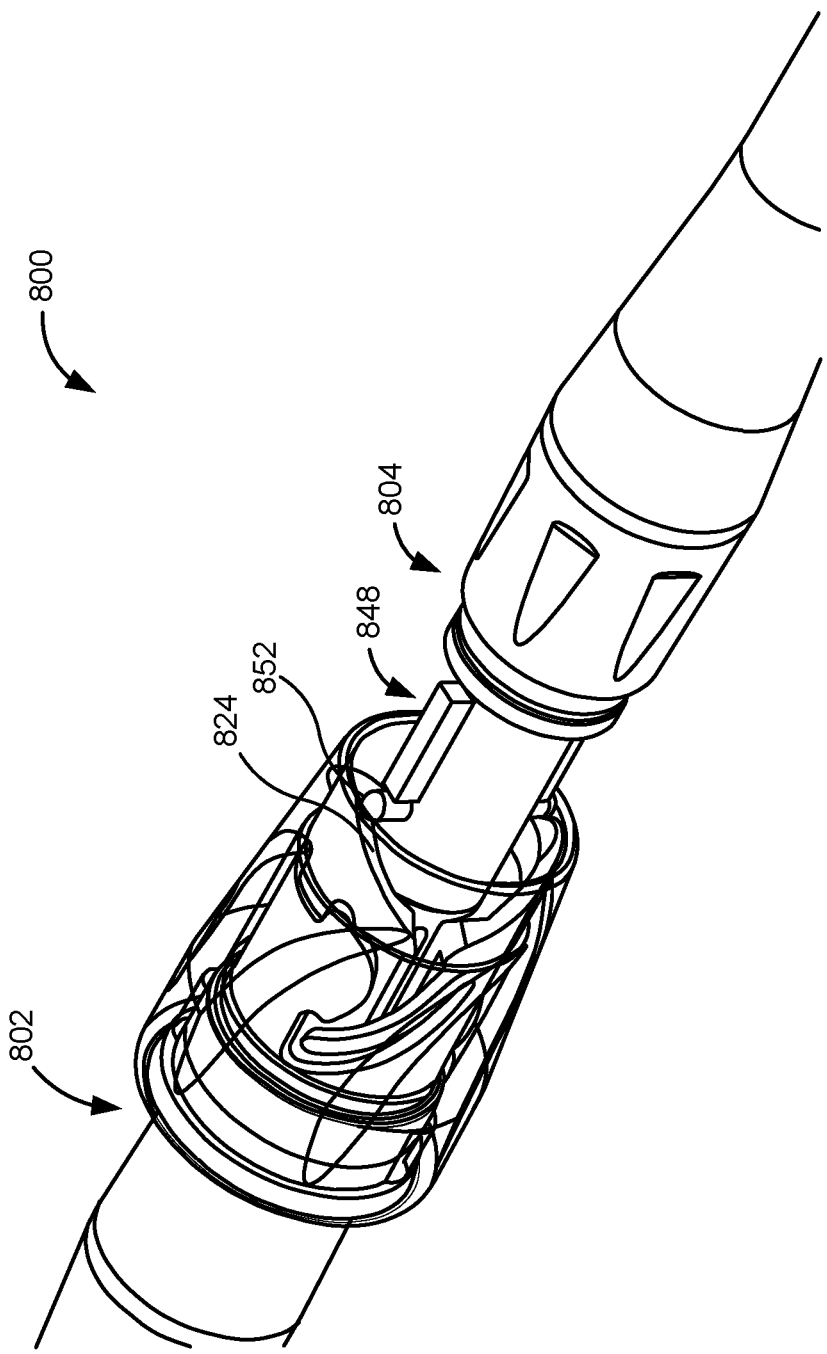
FIG. 14 depicts a first step for connecting the connector system.
Figure 15:
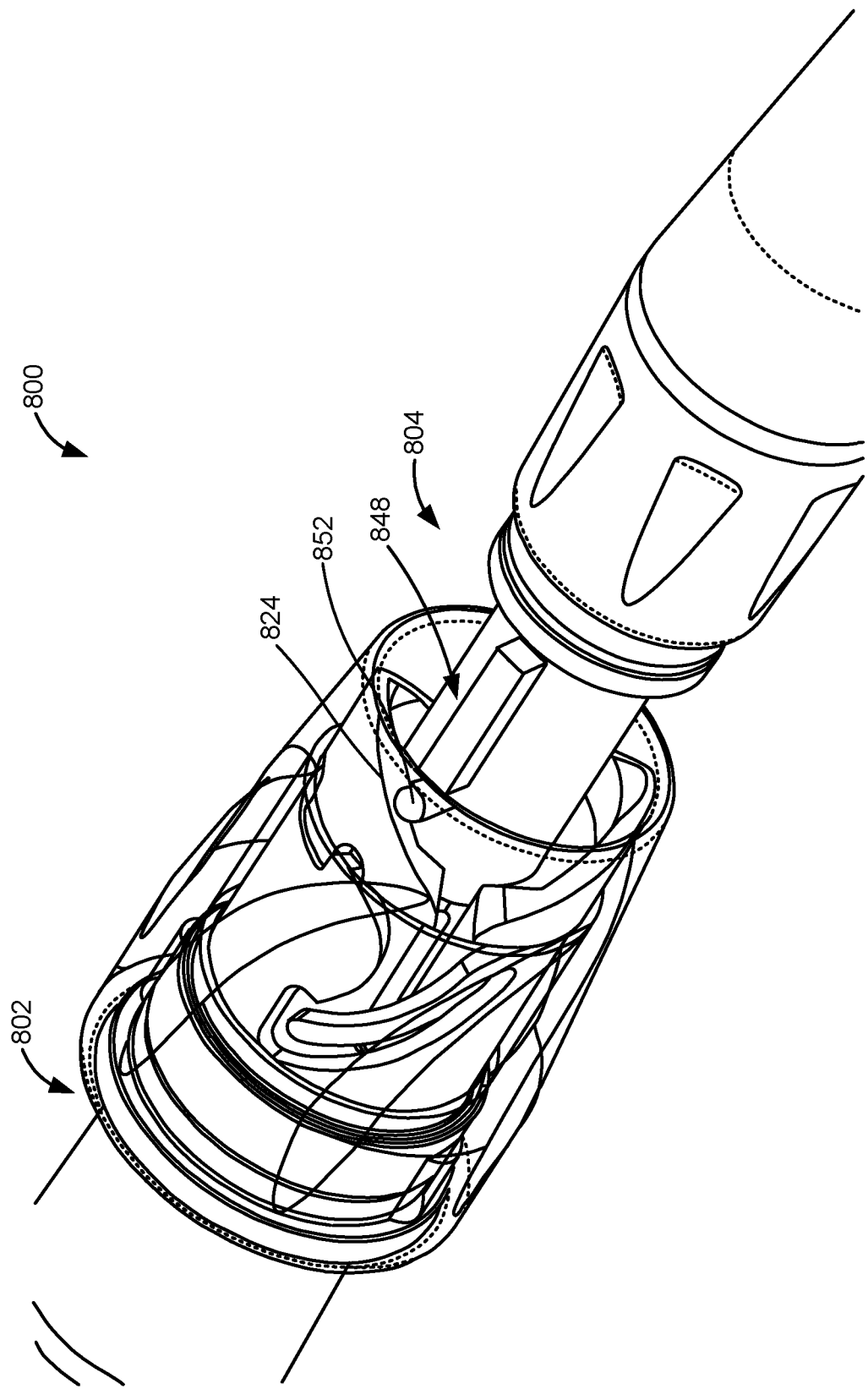
FIG. 15 depicts a second step for connecting the connector.
Figure 16:
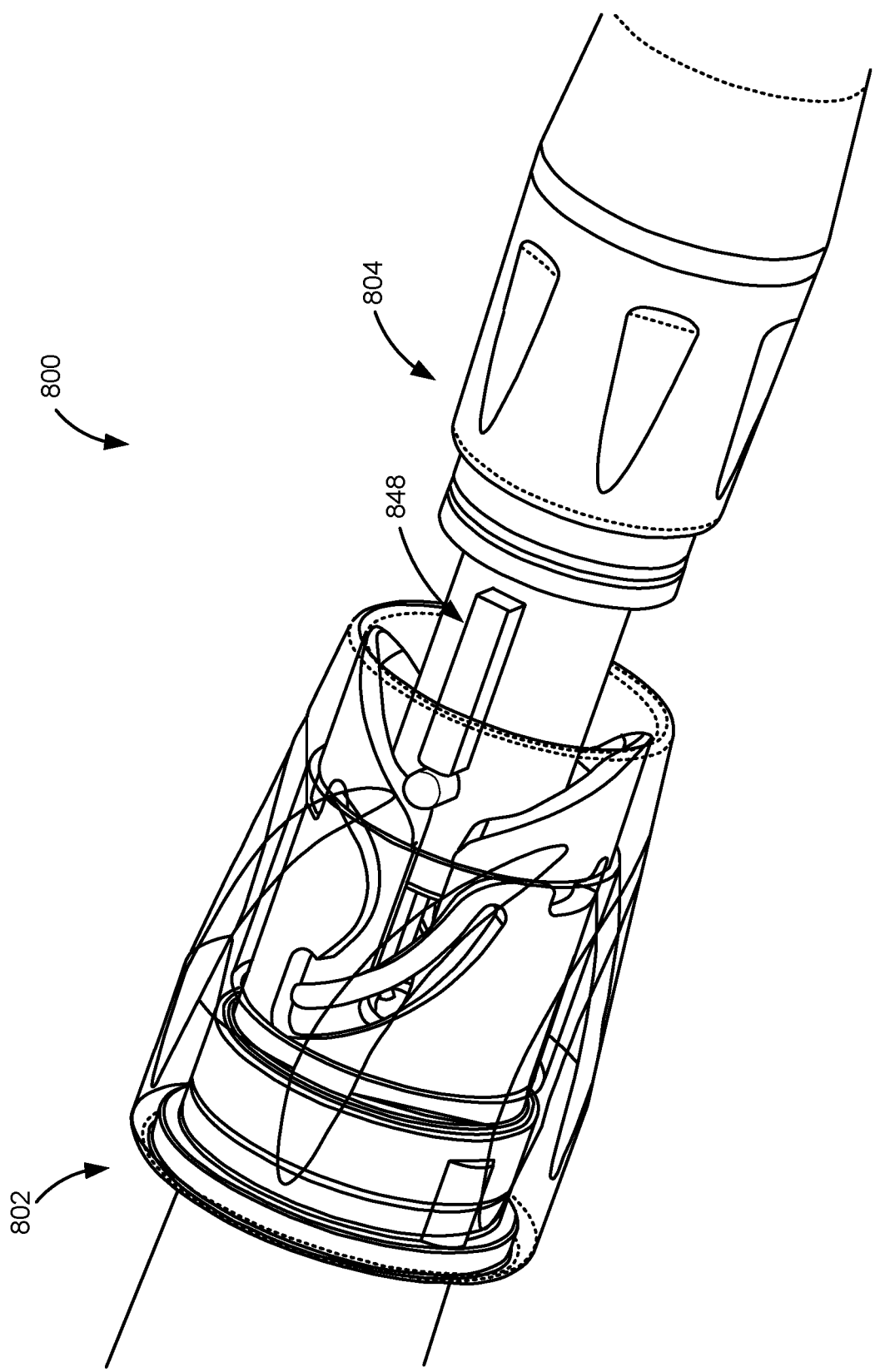
FIG. 16 depicts a third step for connecting the connector.

FIGS. 14 through 20 depict steps in a method of coupling the connector receptacle 802 and the connector insert 804. FIG. 14, is a perspective view of the connector system 800 showing a first step for connecting the connector system 800. As the connector insert 804 is inserted into the connector receptacle 802, the following surface 848, and specifically the circular cylindrical member 852 engages with the mating feature 824, and specifically with the cam surface 826 of the connector receptacle 802. As the connector insert 804 is advanced into the connector receptacle 802, the engagement between the following surface 848 and the mating feature 824 reorients the connector insert 804 with respect to the connector receptacle 802 as shown in FIG. 15, a perspective view of the connector system 800 showing a second step for connecting the connector system 800, and in FIG. 16, a perspective view of the connector system 800 showing a third step for connecting the connector system 800.

Figure 17:
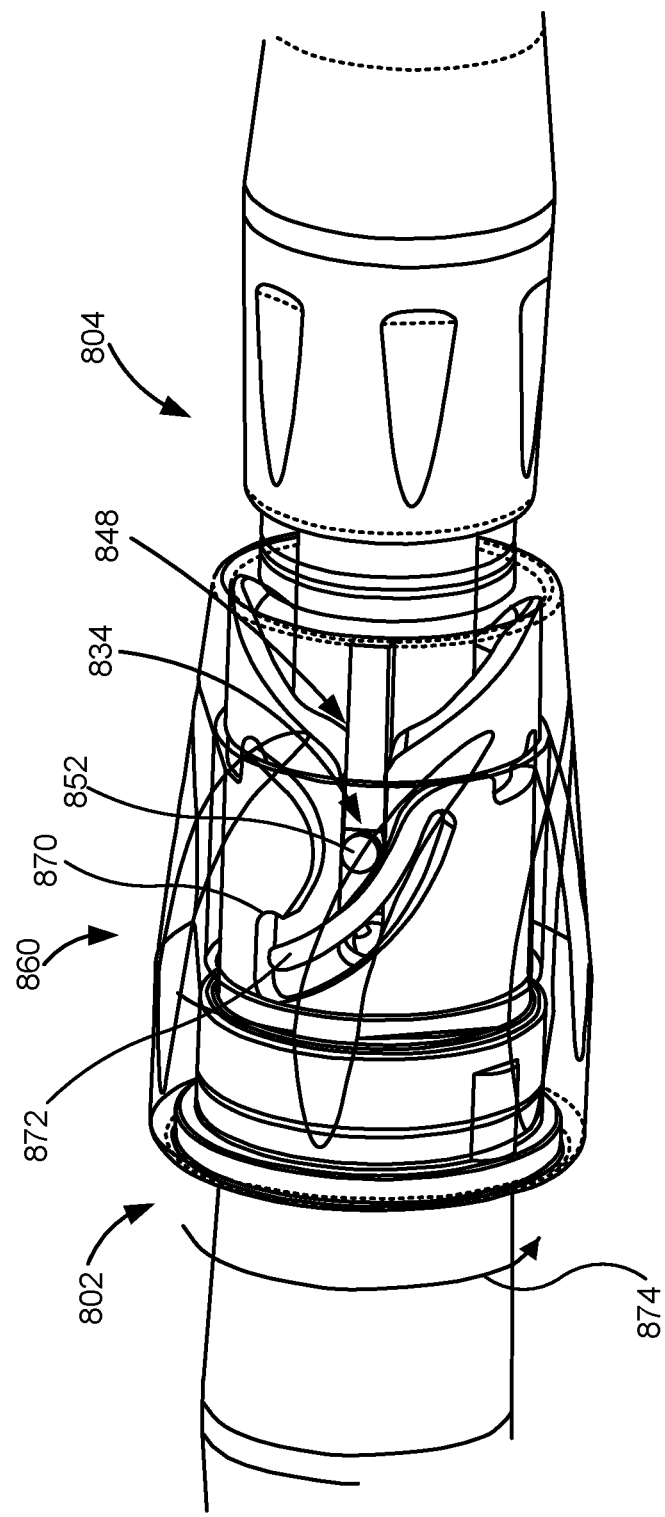
FIG. 17 depicts a fourth step for connecting the connector.

FIGS. 17 through 20 shows steps in the method for connecting the connector insert 804 and the connector receptacle 802 in which the following surface 848 is inserted into and thus received in the follower receptacle 834, and in which the following surface 848 begins to engage and interact with the locking member 860. In some embodiments, the following surface 848 begins to enter the follower receptacle 834 after the connector insert 804 is reoriented to the second orientation with respect to the connector receptacle 802. As shown in FIG. 17, a perspective view of the connector system 800 showing a fourth step for connecting the connector system 800, the connector insert 804 has been reoriented from a first orientation with respect to the connector receptacle 802 to a second orientation with respect to the connector receptacle 802 in which the following surface 848 is aligned with the follower receptacle 834. As further seen in FIG. 17, when the second orientation of the connector insert 804 with respect to the connector receptacle 802, the connector insert 804 can be further advanced into the connector receptacle 802, thereby advancing the following surface 848 into the follower receptacle 834.

In some embodiments, the locking member 860 can comprise a blocking feature 870 configured to engage with at least a portion of the following surface 848, and specifically engage with the circular cylindrical member 852, to prevent retraction of the connector insert 804 from the connector receptacle 802. The locking member 860 can further include a biasing feature 872 that can be configured to engage with at least a portion of the following surface 848 to bias the blocking feature 870 to engage with the at least a portion of the following surface 848 to thereby prevent the decoupling and/or disconnection of the connector insert 804 and the connector receptacle 802. In some embodiments, the biasing feature 872 comprises a compliant member configured to deflect to allow the blocking feature 870 to engage and disengage with the at least a portion of the following surface 848. In the embodiment depicted in FIG. 17, the biasing feature 872 comprises a compliant, cantilevered beam.

In some embodiments, the insertion of the connector insert 804 into the connector receptacle 802, and specifically, the insertion of the following surface 848 into the follower receptacle 834 results in the contacting and engagement of the biasing feature 872 by the following surface 848, which engagement deflects the biasing feature 872 and/or rotates the locking member 860 about the connector receptacle 802 as indicated by arrow 874.

Figure 18:
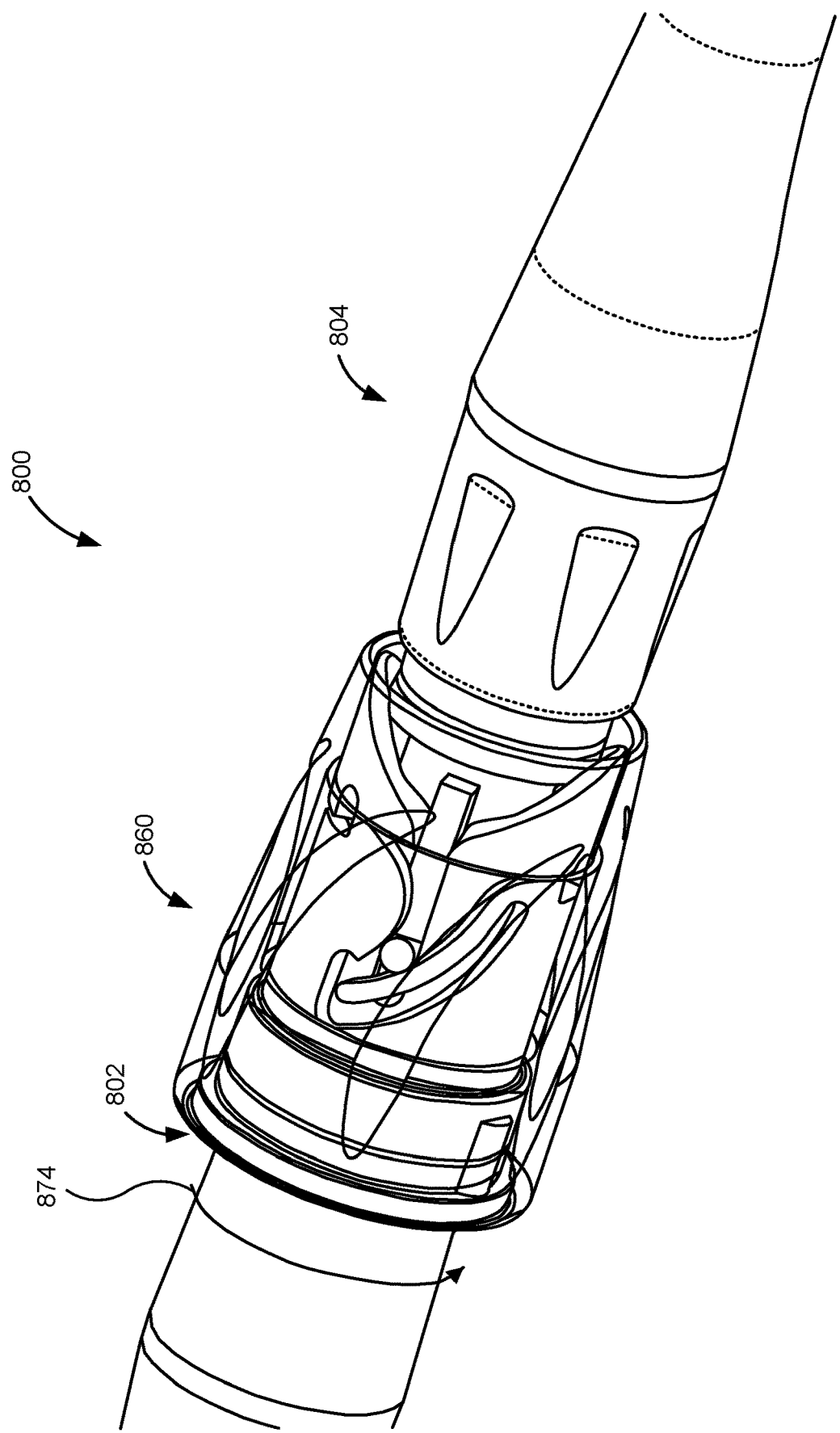
FIG. 18 depicts a fifth step for connecting the connector.
Figure 19:
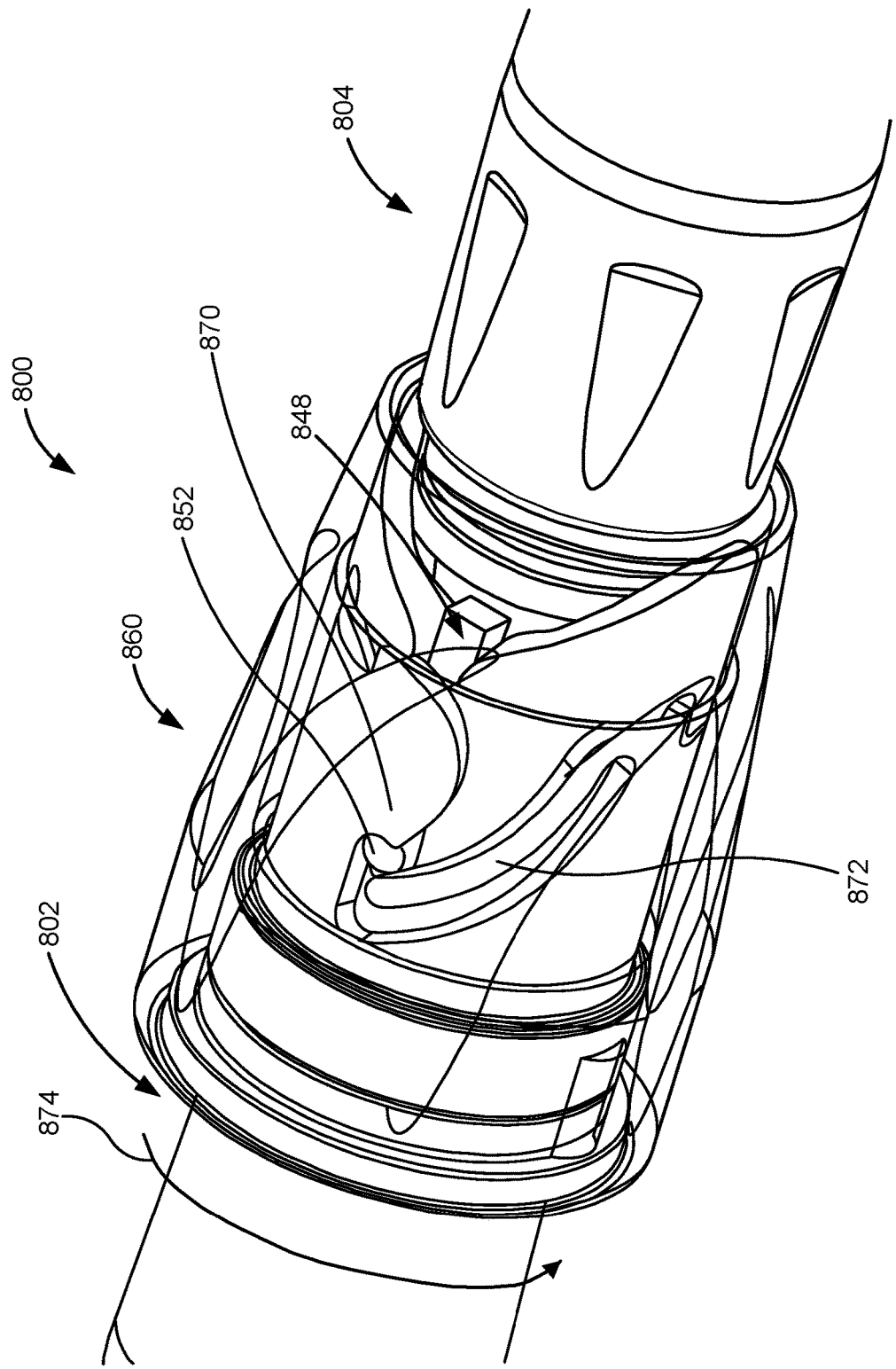
FIG. 19 depicts a sixth step for connecting the connector.

The further insertion of the connector insert 804 into the connector receptacle 802 further rotates the locking member 860 as the following surface 848 further advances into the follower receptacle 834 as shown in FIGS. 18 and 19. Although not seen in the figures, the further advancement of the connector insert 804 into the connector receptacle 802 causes mating of the contacts 822 of the connector receptacle with the insert contacts 846 of the connector insert 804.

Figure 21:
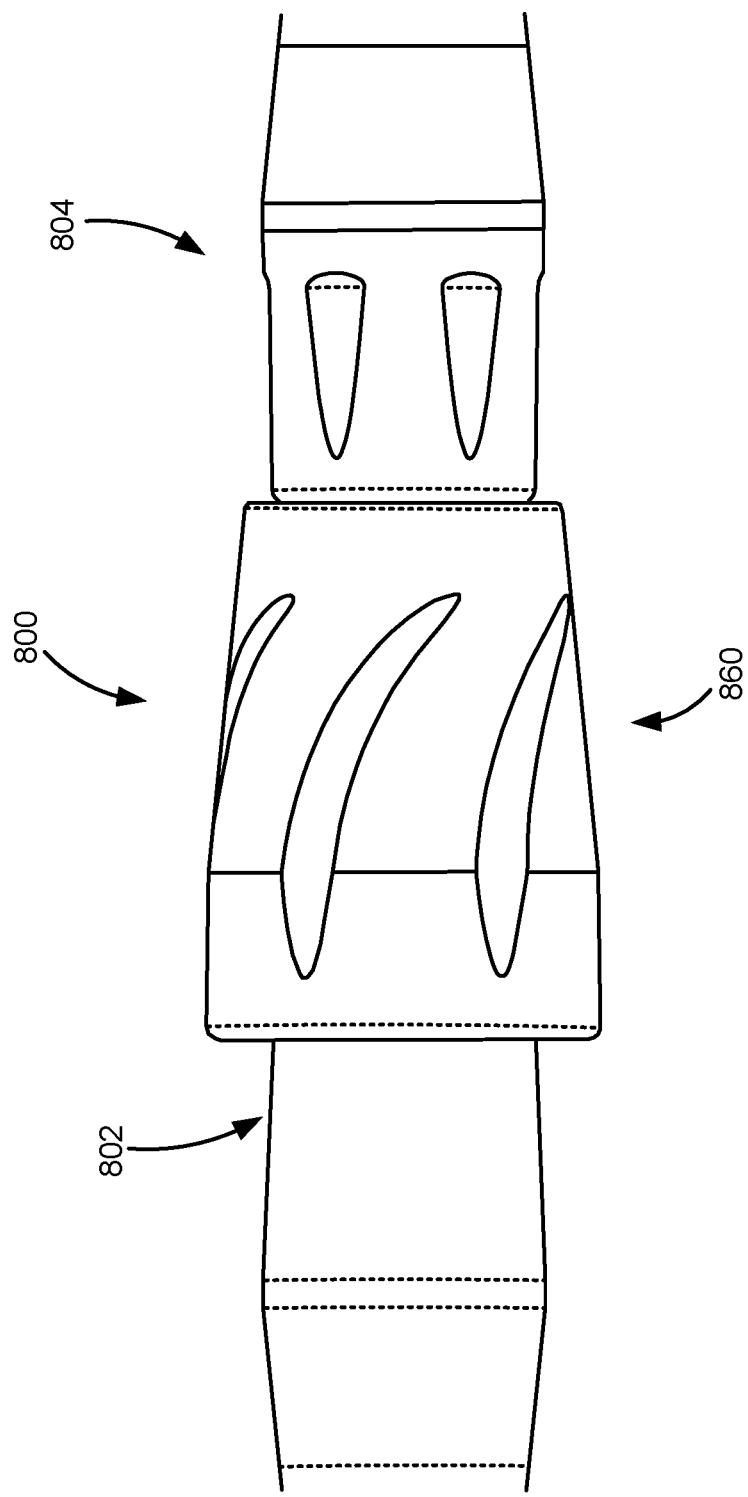
FIG. 21 is a side view of the connector system in a connected configuration.

As seen in FIG. 19, when the connector insert 804 is fully inserted into the connector receptacle 802, a portion of the following surface 848, and specifically the circular cylindrical member 852 engages with the locking member 860, and specifically with the blocking feature 870 to prevent disconnection and/or decoupling of the connector insert 804 and the connector receptacle 802. In some embodiments, and as shown in FIG. 19, the biasing feature 872 applies a force to the portion of the following surface 848, and specifically to the circular cylindrical member 852 to maintain engagement with the blocking feature 870. An embodiment of the coupled connector system 800 is shown in FIG. 21.

In some embodiments, the connector insert 804 and the connector receptacle 802 can be decoupled by rotating the locking member 860 relative to the connector receptacle 802 to disengage the following surface 848, and specifically the circular cylindrical member 852 from the blocking feature 870. Once the following surface 848, and specifically the circular cylindrical member 852 are disengaged from the blocking feature 870, the connector insert 804 can be removed from the connector receptacle 802 to decouple and/or disconnect the connector insert 804 and the connector receptacle 802.

Figure 20:
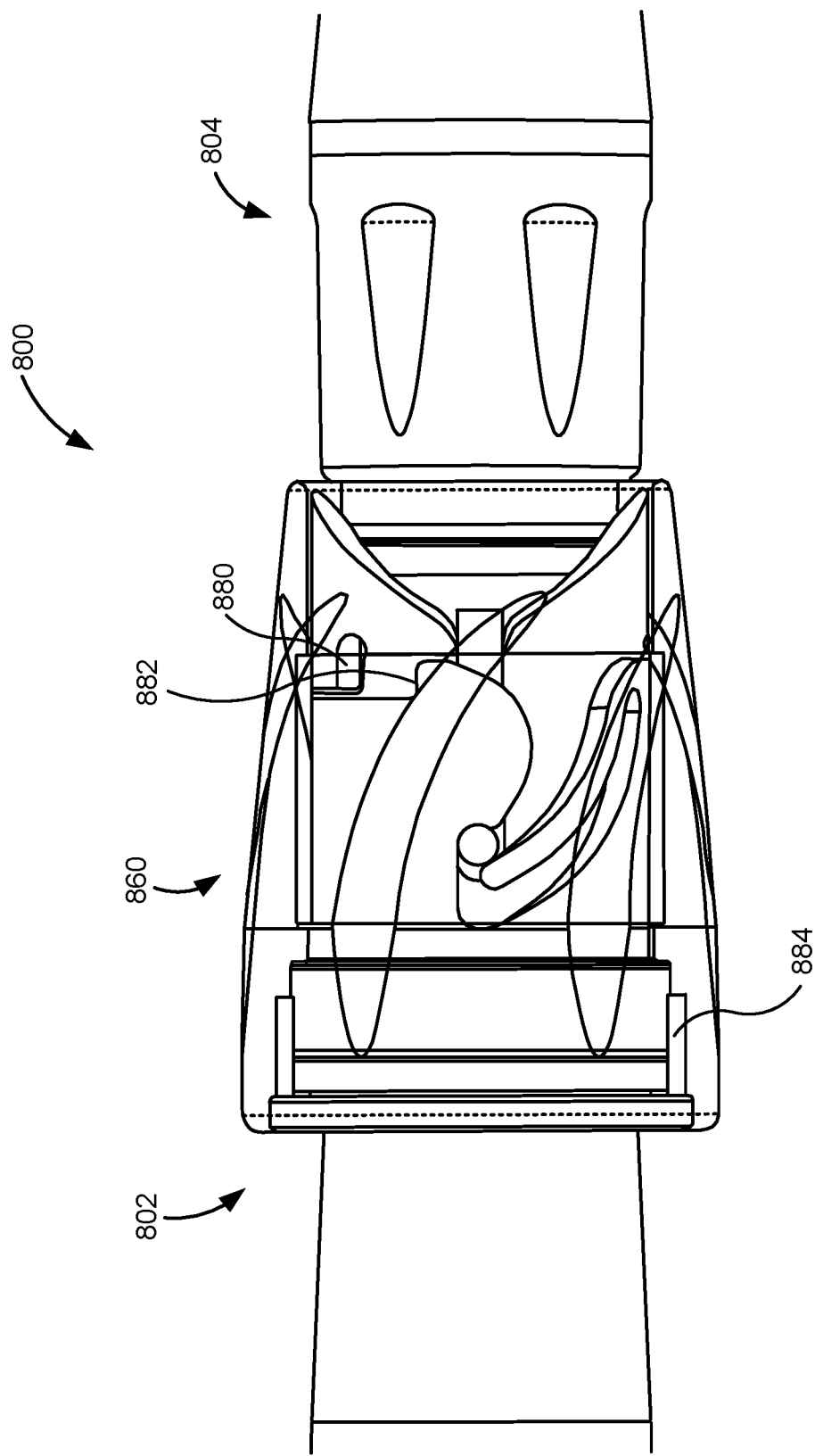
FIG. 20 depicts a seventh step for connecting the connector.

In some embodiments, and as depicted in FIG. 20, the connector receptacle 802 can include one or several limiting features 880 that can engage with abutting features 882 of the locking member 860. In some embodiments, the limiting features 880 and the abutting features 882 can interact to limit rotation of the locking member 860 about the connector receptacle 802. In some embodiments, and as also depicted in FIG. 20, the locking member 860 can be coupled to the connector receptacle 802 via a thrust washer 884, which thrust washer 884 can be polymer.

In the foregoing specification, the invention is described with reference to specific embodiments thereof, but those skilled in the art will recognize that the invention is not limited thereto. Various features and aspects of the above-described invention can be used individually or jointly. Further, the invention can be utilized in any number of environments and applications beyond those described herein without departing from the broader spirit and scope of the specification. The specification and drawings are, accordingly, to be regarded as illustrative rather than restrictive. It will be recognized that the terms "comprising," "including," and "having," as used herein, are specifically intended to be read as open-ended terms of art.

What is claimed is:
1. An implantable blood pump system comprising:
an implantable blood pump;
a controller coupled to the blood pump;
a connector receptacle comprising:
  a plurality of contacts; and
  a following surface comprising a first and a second key; and
a connector insert configured to be received within the connector receptacle to couple a plurality of insert contacts with the plurality of contacts of the connector receptacle, the connector insert comprising:
walls defining a follower receptacle configured to receive a portion of the following surface when the connector insert is in a desired alignment with respect to the connector receptacle; and
a cam surface configured to engage with the following surface to bias the connector insert to the desired alignment with respect to the connector receptacle when the connector insert is inserted into the connector receptacle.

2. The implantable blood pump system of claim 1, wherein the connector receptacle is located in the controller.

3. The implantable blood pump system of claim 1, wherein the connector receptacle is located in blood pump.

4. The implantable blood pump system of claim 1, wherein the connector receptacle comprises a side and a recessed bottom and defines a receptacle volume having an opening, and wherein the following surface extends from the side of the connector receptacle.

5. The implantable blood pump system of claim 4, wherein the first key and the second key have a first pointed tip and a second pointed tip directed towards the opening of the receptacle volume.

6. The implantable blood pump system of claim 1, wherein the cam surface comprises a pair of inclined planes extending around at least a portion of an exterior of the connector insert.

7. The implantable blood pump system of claim 6, wherein each of the pair of inclined planes terminates at one or the walls defining the follower receptacle.

8. The implantable blood pump system of claim 7, wherein the pair of inclined planes comprises a first pair of inclined planes and a second pair of inclined planes.

9. The implantable blood pump system of claim 8, wherein the first pair of inclined planes meet the second pair of inclined planes at a first point and a second point.

10. The implantable blood pump system of claim 9, wherein the cam surface and the following surface are configured such that following surface is at least partially received in the follower receptacle before any of the plurality of insert contacts engage any of the plurality of contacts of the connector receptacle.

11. The implantable blood pump system of claim 10, further comprising a seal extending around the connector receptacle, wherein the seal is configured to seal with the connector insert when the connector insert is received within the connector receptacle.

12. The implantable blood pump system of claim 1, wherein the implantable blood pump system comprises a locking member extending at least partially around the connector receptacle.

13. The implantable blood pump system of claim 12, wherein the locking member comprises a channel in which the connector receptacle is at least partially received.

14. The implantable blood pump system of claim 13, wherein the locking member is rotatable about the connector receptacle.

15. The implantable blood pump system of claim 14, wherein the locking member selectively engages with the following surface of the connector insert to retain the at least a portion of the following surface within the follower receptacle.

16. The implantable blood pump system of claim 15, wherein the following surface further comprises a circular cylindrical member extending from a side of the connector insert.

17. The implantable blood pump system of claim 16, wherein the locking member comprises: a blocking feature configured to engage with at least a portion of the following surface to prevent retraction of the connector insert from the connector receptacle; and a biasing feature configured to bias the blocking feature to engage with the at least a portion of the following surface.

18. The implantable blood pump system of claim 17, wherein the blocking feature engages with the circular cylindrical member.

19. The implantable blood pump system of claim 18, wherein the biasing feature comprises a compliant member configured to deflect to allow the blocking feature to engage and disengage with the at least a portion of the following surface, and wherein the inserting of the connector insert into the connector receptacle deflects the compliant member and rotates the locking member about the connector receptacle.

20. A method of coupling an implantable blood pump system, the method comprising:
   contacting a mating feature of a connector insert to an orientation feature of a connector receptacle, wherein the mating feature comprises a pair of inclined planes wrapping around at least a portion of an exterior of the connector insert;
   advancing the connector insert into the connector receptacle, wherein the connector insert has a first orientation when advanced into the connector receptacle;
   reorienting the connector insert from the first orientation to a second orientation via interaction between the orientation feature of the connector receptacle and the mating feature of the connector insert connector insert as the connector insert advances into the connector receptacle; and
   mating insert contacts with connector contacts.

21. The method of claim 20, wherein the orientation feature comprises a key extending from a side wall into a receptacle volume.

22. The method of claim 21, further comprising receiving a key in a key slot on the connector insert when the connector insert is reoriented to the second orientation.

23. The method of claim 22, wherein the key comprises a pointed key having a point.

24. The method of claim 23, wherein contacting the mating feature of the connector insert to the orientation feature of the connector receptacle comprises contacting the point of the pointed key with the mating feature of the connector insert.

25. The method of claim 22, wherein the pair of inclined planes comprises a first inclined plane having a positive slope and a second inclined plane having a negative slope.

26. The method of claim 25, wherein each of the first inclined plane and the second inclined plane terminates at the key slot.

* * * * *